United States Patent
Gay et al.

(10) Patent No.: US 7,348,161 B2
(45) Date of Patent: Mar. 25, 2008

(54) MACROLIDE EFFLUX GENETIC ASSEMBLY

(75) Inventors: Kathryn Gay, Atlanta, GA (US); David S. Stephens, Stone Mountain, GA (US)

(73) Assignee: Emory University, Atlanta, GA (US)

( * ) Notice: Subject to any disclaimer, the term of this patent is extended or adjusted under 35 U.S.C. 154(b) by 380 days.

(21) Appl. No.: 10/472,801

(22) PCT Filed: Mar. 15, 2002

(86) PCT No.: PCT/US02/09413

§ 371 (c)(1),
(2), (4) Date: Jan. 26, 2004

(87) PCT Pub. No.: WO02/077196

PCT Pub. Date: Oct. 3, 2002

(65) Prior Publication Data

US 2005/0070698 A1 Mar. 31, 2005

Related U.S. Application Data

(60) Provisional application No. 60/278,196, filed on Mar. 23, 2001.

(51) Int. Cl.
*C12Q 1/37* (2006.01)
*C12Q 1/14* (2006.01)
*C07K 14/325* (2006.01)
*C12N 1/20* (2006.01)

(52) U.S. Cl. ............... 435/23.7; 530/350; 435/252.33; 435/7.2; 435/32

(58) Field of Classification Search ............ None
See application file for complete search history.

(56) References Cited

U.S. PATENT DOCUMENTS 5,872,104 A 2/1999 Vermeulen et al. ......... 514/29

(Continued)

FOREIGN PATENT DOCUMENTS

WO 98/49294 11/1998

(Continued)

OTHER PUBLICATIONS

Galye et al, Identification of regions in interleukin-1 alpha important for activity J Biol Chem. Oct. 15, 1993;268(29):22105-11.*

(Continued)

*Primary Examiner*—Sheridan Swope
(74) *Attorney, Agent, or Firm*—Greenlee, Winner and Sullivan, P.C.

(57) ABSTRACT

Macrolide resistance associated with macrolide efflux (mef) in *Streptococcus pneumoniae* has been defined with respect to the genetic structure and dissemination of a novel mefE-containing chromosomal insertion element. The mefE gene is found on the 5'-end of a 5.5 kb or 5.4 kb insertion designated mega (<u>m</u>acrolide <u>e</u>fflux <u>g</u>enetic <u>a</u>ssembly) found in at least four distinct sites of the pneumococcal genome. The element is transformable and confers macrolide resistance to susceptible *S. pneumoniae*. The first two open reading frames (ORFs) of the element form an operon composed of mefE and a predicted ATP-binding cassette homologous to msrA. Convergent to this efflux operon are three ORFs with homology to stress response genes of Tn5252. Mega is related to mefA-containing element Tn1207.1. Macrolide resistance due to mega has been rapidly increased by clonal expansion of bacteria containing it and horizontally by transformation of previously sensitive bacteria.

11 Claims, 6 Drawing Sheets

U.S. PATENT DOCUMENTS

| | | | |
|---|---|---|---|
| 5,989,832 A | 11/1999 | Trias et al. | 435/7.2 |
| 6,020,121 A | 2/2000 | Bao et al. | 435/4 |
| 6,037,123 A | 3/2000 | Benton et al. | 435/6 |
| 6,228,588 B1 | 5/2001 | Benton et al. | 435/6 |

FOREIGN PATENT DOCUMENTS

| | | |
|---|---|---|
| WO | 00/06736 | 2/2000 |
| WO | 01/32882 | 5/2001 |

OTHER PUBLICATIONS

Whisstock et al, Prediction of protein function from protein sequence and structure. Q Rev Biophys. Aug. 2003;36(3):307-40. Review.*

Alonso et al. (Jul. 2000) "*Stenotrophomonas maltophila* D457R Contains a Cluster of Genes from Gram-Positive Bacteria Involved in Antibiotic and Heavy Metal Resistance," *Antimicrob. Agents and Chemother.* 44(7):1778-1782.

Campbell et al. (1998) "A competence regulon in *Streptococcus pnemoniae* revealed by genomic analysis," *Mol. Microbiol.* 27:929-939.

Clancy et al. (1996) "Molecular cloning and functional analysis of a novel macrolide-resistance determinant *mefA*, from *Streptococcus pyogenes*," *Mol. Microbiol.* 22: 867-879.

Clancy et al. (Jan. 1997), NCBI Accession No. SPU70055. *Streptoccus pyogenes* macrolide-efflux protein *(mef)* gene, complete cds.

Claverys et al. (1995) "Construction and evaluation of new drug-resistance cassettes for gene disruption mutagenesis in *Streptococcus pneumoniae*, using an *ami* test platform" *Gene* 164:123-128.

Claverys et al. (1998) "Competence regulons, genomics and steptococci," *Mol. Microbiol.* 29:1125-1127.

Corso et al. (1998) "Molecular Characterization of Penicillin-Resistant *Streptococcus pneumoniae* Isolates Causing Respiratory Disease in the United States," *Microb. Drug resist.* 4:325-337.

Del Grosso et al. (Mar. 2002). NCBI Accession No. AF376746. *Streptococcus pneumoniae* macrolide efflux protein E (*mef*E) and ABC transporter genes, complete cds.

Del Grosso et al. (Mar. 2002) "Macrolide Efflux Genes *mef*(A) and *mef*(E) Are Carried by Different Genetic Elements in *Steptococcus pneumoniae*," *J. Clin. Microbiol.* 40(3):774-778.

Farrell et al. (Oct. 2001) "Detection of macrolide resistance mechanisms in *Streptococus pneumoniae* and *Streptococcus pyogenes* using a multiplex rapid cycle PCR with microwell-format probe hybridization," *J. Antimicrob. Chemotherapy* 48:541-544.

Garvey et al. (Apr. 1997) "Identification of a RecA Homolog (RecA$_{LP}$) on the Conjugative Lactococcal Phage Resistance Plasmid PNP40: Evidence of a Role for Chromosomally Encoded RecA$_L$ in Abortive Infection," *Appl. Environ. Microbiol.* 63(4):1244-1251.

Gasc et al. (1980) "Lack of SOS Repair in *Streptococcus pneumoniae*," *Mutat. Res.* 70:157-165.

Garvey et al. (Apr. 1997) NCBI Accession No. AAB52385. ORFU, *Lactocococus lactis*.

Gay and Stephens (Jul. 2001) "Structure and Dissemination of a Chromosomal Insertion Element Encoding Marolide Efflux in *Streptoccus pneumoniae*," *J. Infect. Dis.* 184:56-65.

Gay and Stephens (Jul. 2001) NCBI Accession No. AF274302. *Steptococcus pneumoniae* insertion sequence macrolide efflux genetic assembly, complete sequence.

Gay et al. (2000) "The Emergence of *Steptococcus pneumoniae* Resistant to Macrolide Antimicrobial Agents: A 6-Year Population-Based Assessment," *J. Infect. Dis.* 182:1417-1424.

Gay and Stephens (2000), "Structure of the *mefE*-Containing Macrolide Efflux Genetic Assembly (Mega) in *Steptococcus pneumoniae*: a Novel Chromosomal Insertion Element," Abstracts of the Interscience Conference on Antimicrobial Agents and Chemotherapy 40:118, Abstract 1929.

Hagman et al. 1997) "The MtrD protein of *Neisseria gonorrhoeae* is a member of the resistance/nodulation/division family constituting part of an efflux system," *Microbiol.* 143:2117-2125.

Hofmann et al. (1995) "The Prevalence of Drug-Resistant *Strepococcus pneumoniae* in Atlanta," *N. Engl. J. Med.* 333:481-486.

Hyde et al. (1990) "Structural model of ATP-binding proteins associated with cystic fibrosis, multidrug resistance and bacterial transport," *Nature* 346:362-365.

Hyde et al. (Oct. 2001) "Marcolide Resistance Among Invasive *Streptocccus pneumoniae* Isolates," *JAMA* 286:1857-1862.

Johnston et al. (1998) "Prevalence and Characterization of the Mechanisms of Macrolide, Lincosamide, and Streptogramin Resistance in Isolates of *Streptococcus pneumoniae*," *Antimicrob. Agents Chemother.* 42:2425-2426.

Kilic et al. (1994) "Identification and Nucleotide Sequence Analysis of a Transfer-Related Region in the Steptococcal Conjugative Transposon Tn5252," *J Bacteriol.* 176:5145-5150.

Kilic et al. (Apr. 1999). NCBI Accession No. L29324. *Streptococcus pneumoniae* integrase, excisionase, repressor protein, relaxase, UmuC MucB homolog, and UmuD MucA homolog genes, complete cds; and unknown genes.

Linton et al. (1998) "The *Escherichia coli* ATP-binding cassette (ABC) proteins," *Mol. Microbiol.* 28:5-13.

Lucas et al. (1995) "Importance of lipooligosaccharide structure in determining gonococcal resistance to hydrophobic antimicrobial agents resulting from the *mtr* efflux system," *Mol. Microbiol.* 16:1001-1009.

Luna et al. (Sep. 2000) "Identification of the Conjugative *mef* Gene in Clinical *Acinetobacter junii* and *Neisseria gonorrhoeae* Isolates," *Antimicrob. Agents Chemother.* 44:2503-2506.

Marchandin (Sep. 2001) "Distrubution of macrolide resistance genes *erm*(B) and *mef*(A) amoung 160 penicillin-intermediate clinical isolates of *Streptococcus pneumoniae* isolated in Southern France," *Pathol. Biol.* 49:522-527.

Martin et al. (1995) "The *rec*A Gene of *Streptococcus pneumoniae* is Part of a Competence-induced Operon and Controls an SOS Regulon," *Dev. Biol. Stand.* 85:293-300.

Martin et al. (1995) "The *rec*A gene of *Streptococcus pneumoniae* is part of a competence-induced operon and controls lysogenic induction," *Mol. Microbiol.* . 15:367-379.

McDougal et al. (1998) "Detection of Tn917-Like Sequences within a Tn916-like Conjugative Transposon (Tn3872) in Erythromycin-Resistant Isolates of *Steptococcus pneumoniae*," *Antimicrob. Agents Chemother.* 42(9):2312-2318.

McDougal et al. (1992) "Analysis of Multiply Antimicrobial-Resistant Isolates of *Streptoccus pneumoniae* from the United States," *Antimicrob. Agents Chemother.* 36:2176-2184.

McEllistream et al. (Jan. 2000) "Simplied Protocol for Pulsed-Field Gel Electrophoresis Analysis of *Streptococcus pneumoniae*," *J. Clin. Microbiol.* 38:351-353.

Mortier-Barriere et al. (1998) "Competence-specific induction of *rec*A is required for full recombination proficiency during transformation in *Steptococcus pneumoniae*," *Mol. Microbiol.*27:159-170.

Munoz-Najar, U. (May 1999) "An Operon that Confers UV Resistance by Evoking the SOS Mutagenic Response in Stepococcal Conjugative Transposon TN5252," *J. Bacteriol.* 181:2782-2788.

Oster et al. (Oct. 1999) "Patterns of Macrolide Resistance Determinants amoung Community-Acquired *Streptoccous pneumoniae* Isolates over a 5-Year Period of Decreased Macrolide Susceptibilty Rates," *Antimicrob. Agents Chemother* 43:2510-2512.

Ozawa, Y. (Dec. 1997). NCBI Accesion No. BAA23799. Structural gene for ultraviolet resistance (*Enterococcus faecalis*).

Pearce et al. (Jan. 1995) "The *rec* Locus, a Competence-Induced Operon in *Streptococcus pneumoniae*," *J. Bacteriol.* 177:86-93.

Perreton (1997) "Antibiotic resistance spread in food," *Nature* 389:801-802.

Rehrauer et al. (Dec. 1998) "Modulation of RecA Nucleoprotein Function by the Mutagenic UmuD'C Protein Complex," *J. Biol. Chem.* 273:32384-32387.

Roberts et al. (Dec. 1999) "Nomenclature for Macrolide and Macrolide-Lincosamide-Streptogramin B Resistance Determinants," *Antimicrob. Agents Chemother.* 43:2823-2830.

Rosato et al. (Jul. 2001) "Inducible Macrolide Resistance on *Corynebacterium jeikeium*" *Antimicrob. Agents Chemother.* 45(7):1982-1989.

Ross et al. (1990) "Indicuble erythromycin resistance in staphlyococci is encoded by a member of the ATP-binding transport super-gene family," *Mol. Microbiol.* 4:1207-1214.

Ross et al. (1996) "Minimal functional system required for expression of erythromycin resistance by *msr*A in *Staphylococcus aureus* RN4220," *Gene* 183:143-148.

Santagati et al. (Sep. 2000) "Characterization of a Genetic Element Carrying the Macolide Efflux Gene *mef*(A) in *Streptococcus pneumoniae*," *Antimicrob. Agents Chemother.* 44:2585-2587.

Santagati et al. (Jul. 2000) NCBI Accession No. AF227520. *Streptocccus pneumoniae* macolide-efflux protein A (*mef*A), ABC-transporter, and UmcC-MucB-like protein genes, complete cds; and unknown genes.

Santagati et al. (Feb. 2002) NCBI Accession No. AF227521. *Streptocccus pyogenes* macolide-efflux protein A (*mef*A), ABC-transporter, and UmuC-MucB-like protein genes, complete cds; and unknown genes.

Shoemaker et al. (Feb. 2001) "Evidence for Extensive Resistance Gene Transfer amoung *Bacteroides ssp.* and amoung *Bacteroides* and Other Genera in the Human Colon," Appl. Environ. Macrobiol. 67:(2)561-568.

Shortridge et al. (1996) "Novel Mechanism of Macrolide Resistance in *Streptococcus pneumoniae*," *Diagn. Microbiol. Infect. Dis.* 26:73-78.

Srinivas et al. (Apr. 1999) NCBI Accession No. L29324. *Streptococcus pneumoniae* integrase excisionase, repressor protein, relaxase, UmuC MucB homolog, and UmuD MucA homolog genes, complete cds; and unknown genes.

Sutcliffe et al. (Aug. 1996) "*Streptococcus pneumoniae* and *Streptococcus pyogenes* Resistant to Macrolides but Sensitive to Clindamycin: a Common Resistance Pattern Mediated by an Efflux System," *Antimicrob. Agents Chemother.* 40(8):1817-1824.

Sutcliffe et al. (Nov. 1996) "Detection of Erythromycin-Resistant Determinants by PCR," *Antimicrob. Agents Chemother.* 40(11):2562-2566.

Swartley et al. (Jul. 1996) "Expression of Sialic Acid and Polysialic Acid in Serogroup *B Neisseria meningitidis*: Divergent Transcription of Biosynthesis and Transport Operons through a Common Promoter Region," *J. Bacteriol.* 178:4052-4059.

Tait-Kamradt et al. (Oct. 1997) "*mef*E is Necessary for the Eryromycin-Resistant M Phenotype in *Streptoccus pneumoniae*," *Antimicrob. Agents Chemother.* 41:2251-2255.

Tait-Kamradt et al. (Dec. 2000) "Two New Machanisms of Macrolide Resistance in Clinical Strains if *Sreptococcus pneumoniae* from Eastern Europe and North America," *Antimicrob. Agents Chemother.* 44(12):3395-3401.

Tait-Kamradt et al. (Jul. 2000). NCBI Accession No. U83667. *Streptococcus pneumoniae* macrolide-efflux determinant (*mef*E) gene, complete cds.

Taniai et al. (Sep. 2003). NCBI Accession No. P04142. Cecropin B Precursor (Lepidopteran A and B).

Vijayakumar, M.N. (Apr. 1999). NCBI Accession No. AAC98439. UmuC MucB homolog (*Steptococcus pneumoniae*).

Waites et al. (May 2000) "Use of Clindamycin Disks to Detect Macrolide Resistance Mediated by *ermB* and *mefE* in *Sreptococcus pneumoniae* isolates from Adults and Children," *J. Clin. Microbiol.* 38:1731-1734.

Walker et al. (1982) "Distantly related sequences in the α- and β-subunits of ATP synthase, myosin, kinases and other ATP-requiring enzymes and a common nucleotide binding fold," *EMBO J.* 1:945-951.

Whittle et al. (Aug. 2001) "Characterization of the 13-Kilobase *ermF* Region of the *Bacteroides* Conjugative Transposon CTnDOT," *Appl. Environ. Microbiol.* 67(8):3488-3495.

Woodgate et al.(1991) "Levels of chromosomally encoded Umu proteins and requirements for in vivo UmuD cleavage," *Mol. Gen. Genet.* 229:10-16.

Wootton et al. (1989) "The Q-linker: a class of interdomain sequences found in bacterial multidomain regulatory proteins," *Protein Eng.* 2:535-543.

Yother et al. (1986) "Transformation of Encapsulated *Streptococcus pneumoniae*," *J. Bacteriol.* 168:1463-1465.

* cited by examiner

FIG. 2

```
ORF5             ----------------------------------------------------------------------------
ORF13/Tn5252     MI------------------------------LRLRLCVMSRADNSAGLILASSPMFKKVFGKSNVGRSYDLPFDVKTRKFSY----YNAKKQGLPTT
ORFU-LL          MTPH----------------------------------------------------------------------------
UvrA-EF          MGIQILNNQFDYSLEPRRAIFFEDVKSNYASIECIERGLNPLTTSLCVMSRADNSNGLTLAASPTFKKVFGMSNVSHSKELPFLVHNRKFNYRLWYKKHTDIFGQT
UmuC-EC          MNLT-----FDYTKEPSRDVFCIDVKSFNASVECVERGLQPLKTMLVVMSNSENSGGLVLAASPMAKKVLGISNVTRKNEVP---------------
                 M---------------DVNAFYASCETVFRP-DLMGKPVVVLSNDGC------VIARNAEAKALGVKMEDP------------WFK-QKDLFRRC

ORF5             ----------------------------------------------------------------LWN-------------------
ORF13/Tn5252     ID----YVRYIEEWAKSTVIVPREWILTIAVNMEIQKIFQDFAAPDDIYPYSIDEGFIDLTSSLNYFVPDKSISRKDKLDIISAAIQKKIWRKTGIYSTVGMSNAN
ORFU-LL          VEPDPKYISEVERWARQTYIVPPQMLIYIKKNLEVINILREITSIDEIHAYSIDESCLDVTESLDFFFPE-ITNTYEQMDKLAQMLQRKIYHKTGLYVTIGMGD-N
UvrA-EF          --DHPNLI----------IVPPRMKLYMKKNQEINNLYNRFVSNEDHSVFSVDESFLDVTASLITYF------KCDTAYKLAKIIQRVIYNHMGLYVTIGIGE-N
UmuC-EC          ----------------GVVCFSSNYELYADMSNRVMSTLEELSPRVEI--YSIDEAFCDLTG------VRNCRDLIDFGREIRATVLQRTHLTVGVGIAQTK

ORF5             ----------------------------------------------------------------GTVALVL---------------
ORF13/Tn5252     PLLAKLALDNEAK--KTPTMRANWSYEDVEKKVWTIPKMTDFWGIGNRMEKRLHNLGITFSIKELAQANPDLIKKELGIMGLELWFHANGIDESNVHKPY-KPKSKG
ORFU-LL          PLLAKLAMDRNYAK--HNTNMRALIRYEDVPSKVWNSISDMTDFWGINVRTEARLNKLGITHSIKELAHADPEMIKRELGVIGLQQFFHANGIDETRLTDKY-KRKSVS
UvrA-EF          PLLAKLALDNEAK--NAPGFVAEWRYEDVPEKVWPISPLTEFCGIGNRMAARLKKLGIRSIYDLAHIEPYMLKERFGIMGLQLYAHSMGIDRSFLGQXAGRPTEKS
UmuC-EC          TL-AKLANHAAKKWQRQTGGVVDLSNLERQRKIMSALPVDDVWGIGRRISKKLDAKGIKTVLDLADTDIRFIRKHFNVV-LERTVRELRGEPCLQLEEFAPTKQEI

ORF5             ----------------------------------------------------------------TTVVSIHIGYSRTEMKKSINA----QNKIEPANLPKPMGESCTCIIPKKYTSGA-VRQIGVSYSGP
ORF13/Tn5252     IGNSQVLPK--DYIKQRDIEIILREMAEQVAVRLRRSGKKATVVSIHLGYSKVEQKRSINT----QMKIEPTNQTALIJNYVLKLFHTKYTSGA-IRNVAVNYSGL
ORFU-LL          FSNSQTLPR--DYTRKSEIGLLINEMAEQVAVRLRKSKKKATNFSLFVGFSMADYKKSLSV--SRKIEPTSSTKDLQEIATRLFNEKYDEGA-VRRLGVSANNL
UvrA-EF          FGNSQVLPK--DYANKEQIKLVLKELSDQVASRLRMASCQTTCVSLFVGYSKGQTDKYGQTGMRRQMKVEPSNWKVLTEHVLRLFEENYAFGVDVRKLGVSYGRL
UmuC-EC          ICSRSFGERITDYPSMRQ--AICSYAARAEKLRSEHQYCRFISTFIKTSPFALNEPYYGNSASVKLLITPTQDSRDIINAATRSLDAIWQAGHRYQKAGVMLGDF

ORF5             VDESYTLLSLFDDVEQIE------KDNRLQTAIDVVREQFGFLAIQKGTVLTEGSRNIERSKLIGGHSAG---GLEGLK
ORF13/Tn5252     VDESFGLISLFDDIEKIE------KEERLQSAIDAIRTEFGFTSLLKGNALDQASRTIARSKLIGGHSAG---GLDGLK
ORFU-LL          IDEPYQLISLFDSDEENEETIKQKDEAVQEALDSIRQKYHFVSVQKATVLKKGSRAVARSKMVGGHSAG---GLEGLN
UvrA-EF          VWNKNLQLDLFPVPEE------QIHETDAYTLIDKIRQKFGFKALIHASSLMEGATAISRASLVGGHAGGTVGLGYTK
UmuC-EC          FSQGVAQLNLFDDNAPRGS------EQLMTVMDTLNAKEGRGTLYFAGQGIQQQWQMKRAMLSPRYTTRSSDLLRVK
```

FIG. 4

A    mega:    5'CATGTT........AGCACA3'

TIGR>SP_66:   5'AAATTC CACATCACGCAA3'
                         C
              Phosphomethlpyrimidine kinase
              *Bacillus subtilis* (1e$^{-41}$)

B    mega:    5'CATGTT........AGCACA3'

TIGR>SP_101:  5'AGACAGGCCTGCCTGATA3'
              DNA-3-methyladenine glycosidase
              *Haemophilus influenzae* (8e$^{-49}$)

C    mega:    5'CATGTT........AGCACA3'

TIGR>SP_15:   5'CAAACAACCCACATTGAAT3'
                                  G
              CAPD protein
              *Staphylococcus aureus* (1e$^{-116}$)

D    mega:    5'CATGTT........AGCACA3'

TIGR>SP_28:   5'CAAACGCAT/AATCATAAT3' TIGR>SP_189
              yerS
              Similar to RNA methyltransferase
              *Bacillus subtilis* (1e$^{-106}$)

MACROLIDE EFFLUX GENETIC ASSEMBLY

CROSS REFERENCE TO RELATED APPLICATIONS

This application is filed under 35 U.S.C. 371, based on PCT/US02/09413, filed Mar. 25, 2002, which claims benefit of U.S. Provisional Application 60/278,196, filed Mar. 23, 2001.

ACKNOWLEDGMENT OF FEDERAL RESEARCH SUPPORT

This invention was made, at least in part, with funding from Centers for Disease Control and Prevention (H50/CCH413121) and the Department of Veteran Affairs (Merit Review Grant). Accordingly, the United States Government has certain rights in this invention.

BACKGROUND OF THE INVENTION

The field of the present invention includes molecular biology, in particular, with respect to the genetics and molecular mechanism of antibiotic resistance, especially macrolide resistance, in bacteria, and to methods for identifying inhibitors of macrolide resistance, in particular, that resistance to macrolides and/or streptogramins due to efflux systems.

Infections caused by Gram positive bacteria including but not limited to *Streptococcus pneumoniae* remain a devastating and worldwide health problem. The treatment of infections due to *S. pneumoniae* has become increasingly complicated due to the rapid emergence of resistance to penicillin. While macrolides (including, but not limited to, erythromycin, clarithromycin, azithromycin) are considered alternatives to penicillin for non-meningeal infections, resistance has rapidly emerged to these agents as well.

There are two known mechanisms of macrolide resistance in *S. pneumoniae*, target modification and macrolide efflux. The pneumococcal ermAM gene product, methylates highly conserved adenine residues in the peptidyl transferase center of newly synthesized 23S rRNA [6]. This methylation blocks the binding of macrolides, lincosamides and streptogramins B, thereby conferring the $MLS_B$ phenotype of antibiotic resistance [7]. The pneumococcal ermAM gene is associated with conjugative transposons that co-harbor other antimicrobial resistance determinants, e.g., tetM [8]. Until 1996 the only known form of macrolide resistance in pneumococci was due to a methylase (the ermAM gene product) which methylates highly conserved adenine residues in the peptidyl transferase center, domain V, of newly synthesized 23S rRNA. This methylation blocks the binding of macrolides, lincosamides and streptogramin B. The expression of this $MLS_B$ phenotype can be inducible or constitutive. There are at least eight classes of erm; ermA, B and C are found on the transposons found in several clinically important pathogens. The pneumococcal ermAM gene is associated with large conjugative and composite transposons, which coharbor other antimicrobial resistance determinants, e.g., tetM and cat. The ermAM gene is very similar to ermB [2, 24]; ermA and C have not been described in *S. pneumoniae*. Erythromycin MICs for pneumococci containing ermAM are typically=64 µg/ml. In certain other organisms, inactivation is an additional potential mechanism.

In 1996, a newly detected macrolide efflux mechanism, mefE, was identified in macrolide-resistant strains of *S. pneumoniae* lacking an ermAM determinant [9]. Pneumococcal strains containing mefE were reported to express resistance only to 14- and 15-membered macrolides (M phenotype). A 3.7 kb pneumococcal fragment containing mefE when cloned in *E. coli* was reported to encode a proton motive force-driven transporter sufficient to confer the M phenotype [10]. mefE and the related determinant mefA, originally described in *S. pyogenes*, are ~90% identical and have been placed in a single class of macrolide efflux genes [11,12]. Both mefE and mefA are now found in *S. pneumoniae* [13,14] and are known to be transferable [15].

In Europe, the ermAM determinant is reported to account for recent increases in macrolide resistance of *S. pneumoniae* while mefA and mefE are found less often [16]. In contrast, most macrolide-resistant pneumococcal strains in North America harbor mefE [13,17-19]. In metropolitan Atlanta, between 1994 and 1999, macrolide resistance of invasive pneumococcal isolates increased from 16.4% to 31.5% [13]. By 1999, mefE was found in 26% of all invasive *S. pneumoniae* isolated in metropolitan Atlanta [13].

There is a need in the art for an understanding of the mechanisms of antibiotic resistance and the spread thereof, and for methods for identifying inhibitors of resistance mechanisms as well as for identifying compounds which evade the resistance mechanisms to allow for efficacious treatment of infectious diseases of bacterial origin.

SUMMARY OF THE INVENTION

The present invention provides a novel genetic element, i.e., the macrolide efflux genetic assembly (mega), derived originally from erythromycin-resistant *Streptococcus pneumoniae*. The nucleotide sequence of a specifically exemplified mega element is provided in SEQ ID NO:1, and the amino acid sequences of the proteins encoded by the ORFs therein are given in SEQ ID NO:2-6. SEQ ID NO:2 is the amino acid sequence of a macrolide efflux protein (MefE), and SEQ ID NO:3 is the amino acid sequence of a macrolide and streptogramin B efflux protein (Mel). SEQ ID NOs:4-6 are the amino acid sequences of proteins having significant sequence identity to proteins of conjugative transposons from Gram positive bacteria. The sequences can be used to identify the present of macrolide and or macrolide and streptogramin resistance in a bacterial strain or they can be used in epidemiological studies, for example, to follow the spread of antibiotic resistance.

The present invention further provides methods for identifying inhibitors of the MefE and/or Mel efflux proteins. The methods involve determining the growth of a bacterium which produces a MefE and/or a Mel protein. When the bacterium is grown in the presence of a subinhibitory (but non-zero concentration of a macrolide), the bacterium contains a low level of the macrolide in the cytoplasm, without growth inhibition. If there is a compound present in the growth medium which inhibits the efflux protein(s), the concentration within the bacterium rises, and growth is inhibited. Desirably, the macrolide efflux protein is the MefE protein of mega as specifically exemplified herein and the macrolide and streptogramin B efflux protein is the Mel protein of mega as specifically exemplified herein. The mega-containing strain and strains containing derivatives of mega in which either the MefE or the Mel coding sequences have been functionally inactivated (for example, by deleting at least one half of the coding sequence of interest) are tested to determine the subinhibitory concentration of a macrolide and/or a streptogramin. Then test compounds are incorporated in the growth medium in addition to the macrolide and/or streptogramin at varying concentration. A control medium contains the test compounds to verify that those test compounds alone do not inhibit growth of the bacteria. Where the test compound results in inhibition of growth only in the presence of a subinhibitory concentration of a macrolide, there is a conclusion that the test compound causes inhibition of the efflux mechanism.

The present invention further provides nucleotide sequences which can be used to predict antibiotic resistance in gram positive infections, for example, those caused by streptococcal, enterococcal or staphylococcal pathogens. Lactococci may also harbor mega and serve as reservoirs of antibiotic resistance which can be transmitted to other Gram positive bacteria, including bacilli, clostridia and various pathogenic microorganisms. The mega-derived mefE nucleotide sequences are characteristic of macrolide resistance (erythromycin, clarithromycin, azithromycin, for example). The presence of mega-derived mel sequences are indicative of resistance to macrolides and streptogramin B antibiotics (including but not limited to dalfopristin and quinupristin). Nucleotides derived in sequence from the 5' and 3' termini of mega can be used to determine the presence of the mega element. Bacterial isolates cultured from patient specimens or patient specimens can be used to test for the presence of these characteristic sequences. Nucleic acid molecules, especially single-stranded nucleic acid molecules, which are derived in sequence from SEQ ID NO:1, can be incorporated into PCR assays for related sequences or they can be incorporated into DNA:DNA hybridization assays or RNA:DNA hybridization. Microarray/microchip technology is particularly suited for use in the detection of mega and/or the prediction of antibiotic resistance in a patient infected with a Gram positive microorganism, especially a Gram positive coccus, and as particularly appropriate to such screening and detection, a streptococcal pathogen, e.g., *S. pyogenes* or *S. pneumoniae*.

As a further aspect of the present invention, the mega element of the present invention can also serve as a "carrier" for the introduction of heterologous DNA into a streptococcal strain, by inserting the DNA of interest into a region of the element not essential for incorporation into the streptococcal genome (or for selecting for its presence). As an alternative to introducing an antibiotic resistance, one can readily delete the mefE and mel sequences and replace them with another selectable marker or replace with a marker for whose expression there is a convenient screen, such as a luciferase coding sequence expressible in the *streptococcus* or a beta-galactose, beta-glucuronidase, etc. For example, a coding sequence for an antigen of interest operably linked to a promoter expressible in a streptococcal strain can be introduced so that the genetically modified strain can produce the antigen of interest and serve as a vaccine, especially where the streptococcal strain is nonpathogenic or attenuated with respect to virulence while maintaining the ability to colonize a human or animal of interest.

BRIEF DESCRIPTION OF THE DRAWINGS

FIG. 2 illustrates alignment of MEL (mega ORF2; see also SEQ ID NO:3) and the macrolide efflux-associated protein MsrA (from *S. epidermidis*; see also SEQ ID NO:32).

FIG. 4 illustrates alignment of mega ORF5 with ORF13 of Tn5252 (AAC98439), ORFU of *L. lactis* (AAB52385), UvrA of *E. faecalis* (BAA23799) and UmuC of *E. coli* (P04152). ORF 5 of mega, ORF13 of Tn5252, ORFU, UvrA and UmuC correspond to the amino acid sequences given in SEQ ID NO: 6, SEQ ID NO:7, SEQ ID NO:8, SEQ ID NO:9 and SEQ ID NO:10, respectively.

FIGS. 5A-5D illustrate Mega insertion sites. FIG. 5A: Class I insert site (e.g., GA3488) CACAT is duplicated at the ends of the mega insert; The 5' and 3' flanking sequences are given in SEQ ID NOs:11 and 12. FIG. 5B: Class II insert site (e.g., GA2551) CT is missing in the chromosomal sequence containing mega; The 5' and 3' flanking sequences are given in SEQ ID NOs:13 and 14. FIG. 5C: Class III insert site; The 5' and 3' flanking sequences are given in SEQ ID NOs. 15 and 16, and FIG. 5D: Class IV insert site; The 5' and 3' flanking sequences are given in SEQ ID NOs. 33 and 34.

DETAILED DESCRIPTION OF THE INVENTION

Figure 1:
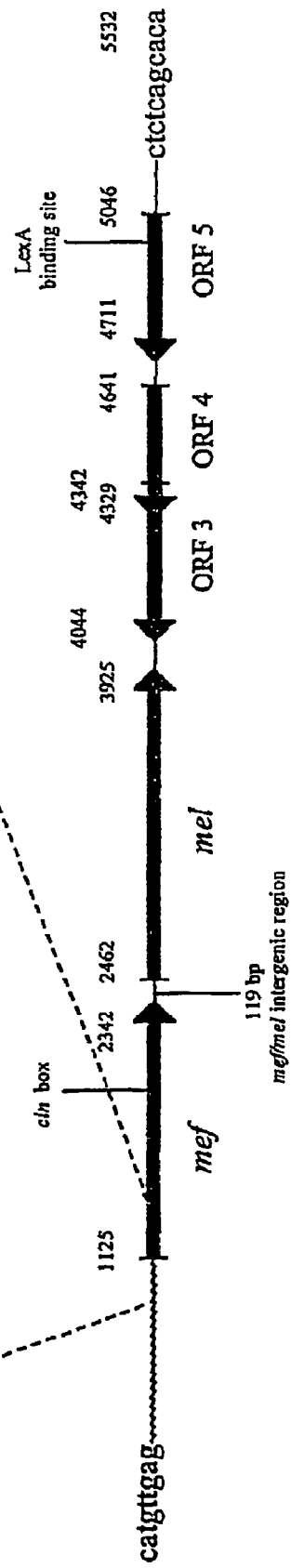
FIG. 1 illustrates the genetic organization of mega in *S. pneumoniae* strain GA3488, insert Class I. The sequence of mega insert Class II is identical except that the mef/mel intergenic region is truncated by 99 bp. Inset: Nucleotide sequence of the first 180 bases of mega ORF1 with the predicted promoter region and the amino acid sequence of mefE. These sequences are found within SEQ ID NO:1 and to amino acids 1-60 of SEQ ID NO:2. A Shine-Dalgarno sequence is boxed. Lines are drawn over predicted −35 and −10 promoter sequences.

Abbreviations used herein include mega, macrolide efflux genetic assembly; ORF, open reading frame; ABC, ATP-binding cassette; cin, competence-induced; single specific primer-polymerase chain reaction, SSP-PCR; pulsed field gel electrophoresis, PFGE. The amino acids which occur in the various protein amino acid sequences referred to in the specification have their usual three- and one-letter abbreviations routinely used in the art: A, Ala, Alanine; C, Cys, Cysteine; D, Asp, Aspartic Acid; E, Glu, Glutamic Acid; F, Phe, Phenylalanine; G, Gly, Glycine; H, His, Histidine; I, Ile, Isoleucine; K, Lys, Lysine; L, Leu, Leucine; M, Met, Methionine; N, Asn, Asparagine; P, Pro, Proline; Q, Gln, Glutamine; R, Arg, Arginine; S, Ser, Serine; T, Thr, Threonine; V, Val, Valine; W, Try, Tryptophan; Y, Tyr, Tyrosine.

Transformation is the major mechanism of horizontal genetic exchange in pneumococci. The discovery that DNA was the molecule responsible for the exchange of genetic information was first made by observing the process of natural transformation in *S. pneumoniae*. Transformation involves uptake of exogenous DNA and subsequent homologous recombination into the recipient chromosome. In pneumococci, competence for transformation occurs in exponential phase growth at a critical cell density. Changes in penicillin binding proteins due to transformation appear to be responsible for the emergence of penicillin resistance in pneumococci. In order for pneumococci to be competent for transformation, a 17 amino acid peptide, competence-stimulating peptide (CSP), is expressed during exponential growth. The gene encoding CSP, comC, encodes a 41 amino acid pre-peptide which is processed to an active heptadecapeptide. This peptide is transported early in competence by the products of the comAB locus. ComC acts as an extracellular signaling molecule, while ComD and ComE are thought to act as a sensor kinase and response regulator, respectively, during early events in transformation.

Transposition and transduction also occur in S. pneumoniae. Conjugative transposons insert in the genome by a site-specific recombination mechanism similar to λ phage and are able to excise and transfer from diplococcus to diplococcus by cell-to-cell contact. These elements are large (>18 kb) and may carry multiple antibiotic resistance markers. Examples are Tn916, Tn5253, Tn1545, Tn3701 and Tn3872. Sometimes these elements are composites (e.g., Tn5253 is a composite of Tn5251, a Tn916-like element, and Tn5252, a 47.5 kb conjugative transposon element [Kilic et al. (J. Bacteriol. 1994. 176:5145-5150], and Tn3872 contains Tn917-like elements inserted into ORF9 of a Tn916-like element). One third of adult clinical isolates and half of the pneumococci recovered from children may harbor bacteriophages. DNA-damage induces temperate bacteriophage thereby causing the lysis of pneumococci.

The SOS system is a bacterial regulatory network induced by DNA damage. The system has been extensively studied in E. coli, but exists in a variety of bacterial species. In E. coli, exposure to a variety of agents or conditions that cause DNA damage (e.g., UV irradiation and quinolone antibiotics such as nalidixic acid) induce over 20 genes in operons referred to as damage inducible (din) genes. RecA and LexA proteins control the expression of these genes.

In S. pneumoniae, the SOS repair system is different. Gasc et al. Mutat. Res. (1980) 70:157-160 observed that pneumococci lacked error-prone repair following UV irradiation or thiamine starvation suggesting the organism did not have a SOS repair system. DNA repair following damage induced by these pathways is dependent on functional UmuDC proteins (see below) which may not be present in all pneumococci. Martin et al. found a SOS repair system in pneumococci that involved RecA and overlapped with the regulation of competence [Martin et al. Devel. Biol. Standardization (1995) 85:293-300].

RecA is encoded as part of the competence-inducible (cin) operon described in S. pneumoniae [Martin et al. Molec. Microbiol. 15:367-379], and is increased three- to five-fold at competence of S. pneumoniae [Pearce et al. J. Bacteriol. (1995) 177:86-93; Mortier-Barriere et al. Molec. Microbiol. (1998) 27: 159-170]. The activated form of RecA, RecA*, appears to be required for homologous recombination, phage induction and SOS mutagenesis repair in pneumococci. Activation of RecA to RecA*, occurs in the presence of single-stranded DNA. By forming a nucleoprotein filament with single-stranded DNA, RecA provides a scaffold for recombination events. Transformation efficiencies in pneumococcal mutants containing a transcriptionally uncoupled RecA operon were reported to be reduced up to 45-fold, and establishment of plasmids was reduced 129-fold [Mortier-Barriere et al. (1998) supra]. RecA* can also inactivate or is postulated to inactivate LexA and LexA-related phage repressors thereby causing the expression of genes involved with stress responses and phage induction.

In E. coli, LexA acts as to repress genes by binding to a conserved motif in the upstream promoter sequences. RecA* inactivates LexA, triggering its autodigestion and producing the derepression of din genes, including DNA polymerase II and in E. coli the umuDC operon. UmuD is activated by RecA to UmuD' which forms a homodimer that combines with UmuC to create a Umu(D')$_2$C complex. This complex acts as an accessory factor for the error-prone, replicative bypass of DNA lesions by DNA polymerase III [Woodgate et al. Molec. Gen. Genet. (1991) 229:10-16]. Recently, the Umu(D')$_2$C complex was demonstrated to inhibit the homologous recombinatory function of RecA and competitively inhibit LexA [Rehrauer et al. J. Biol. Chem. (1998) 273:32384-32387]. The TIGR database for S. pneumoniae contains a RecA-like and a possible UmuC, but no significant homologues for UmuD. However, ORF 13 and 14 in the pneumococcal conjugative transposon Tn5252 can function as umuDC homologues (GenBank, accession L29324) [Swartley et al. J. Bacteriol. (1996) 178:4052-4059].

In gram-negative bacilli, RecA* also induces lysogeny through cleavage of the LexA-related repressors of bacteriophages and other mobile elements e.g., P22, coliphage 186, retro phage R86, element e14 and Tn5. The mechanisms of phage integration and excision in S. pneumoniae are poorly understood. However, pneumococcal phage integration occurs in a site-specific manner [Romero et al. J. Virol. (1992) 66:2860-2864; Martin et al. Virology (1995) 211:21-32]. Mutants deficient in recA are unable to induce prophage and cell lysis, whereas recA-containing pneumococci are lysogenic even in the absence of mitomycin C. Transformation increases lysogeny by elevating RecA levels. Taken together, the data indicate the presence of a SOS response in S. pneumoniae and a role of RecA in this response, as well as in transformation and in the movement of mobile genetic elements.

Pneumococcal infections and the rapid emergence of antibiotic resistance in S. pneumoniae are major concerns in infectious diseases and public health. The mechanisms of spread of pneumococcal antibiotic resistance in the population are not completely understood. The studies proposed are significant in defining the genetic basis of the emergence of macrolide resistance in S pneumoniae and the spread of the determinant in a human population. The work also has application to understanding novel means of horizontal gene transfer, in particular, how competence, illegitimate recombination and the SOS stress response contribute to the spread of genetic elements.

Infections due to S. pneumoniae are a major problem in the aging and immunocompromised veteran population, especially those with COPD, heart disease, diabetes, HIV/AIDS, splenectomy, sickle cell disease and cancer. The rapid emergence of antibiotic resistance has compromised the ability to treat S. pneumoniae infections in these and other patients. The pathogenic streptococci are important etiological agents for septicemia, bacterial meningitis, pneumonia, sinusitis and otitis, and in the re-emergence of pneumococcal endocarditis and osteomyelitis. Understanding the mechanisms of emergence of macrolide resistance may allow more directed approaches to the treatment, prevention and control of S. pneumoniae infections in veteran and other patient populations.

Erythromycin-resistant isolates of S. pneumoniae recovered from patients with invasive pneumococcal disease in metropolitan Atlanta and confirmed by PCR to contain mefE were studied. Southern hybridizations using a mefE probe, SmaI digestion and performed on fifteen randomly chosen of these erythromycin-resistant isolates indicated that mefE was present as a single band. A 5532 bp element containing mefE was defined in pneumococcal isolate (GA3488) recovered from a patient with pneumococcal bacteremia in 1995 (FIG. 1, SEQ ID NO:1). The complete genetic element was designated as mega (macrolide efflux genetic assembly) (GenBank accession no. AF274302). The nucleotide sequence was delineated by gene walking from either end of mefE with SSP-PCR, and confirmed by automated DNA sequencing of multiple overlapping PCR products. Sequence analysis confirmed the absence of a SmaI site.

The 5' nucleotide sequence of mega was a 944 bp (33.8% GC content) region with no predicted ORF or significant homology to nucleotide or amino acid entries in the GenBank database. The 5' 180 bp immediately preceding mefE in mega, however, was identical to the sequence preceding mefA in Tn1207.1 (GenBank accession No. AF227520) and mefA in *Streptococcus pyogenes* (GenBank accession No. SPU7005), and included a putative promoter region (FIG. 1 inset) [10]. The open reading frame (ORF) which demonstrated >99% sequence homology to mefE (GenBank accession no. U83667) began at nucleotide 1125 of mega. The complementary strand of the mefE ORF contained a potential competence-induced (cin) box (TACGAATA). The amino acid sequence of the mega MefE protein is given in SEQ ID NO:2.

Figure 2:
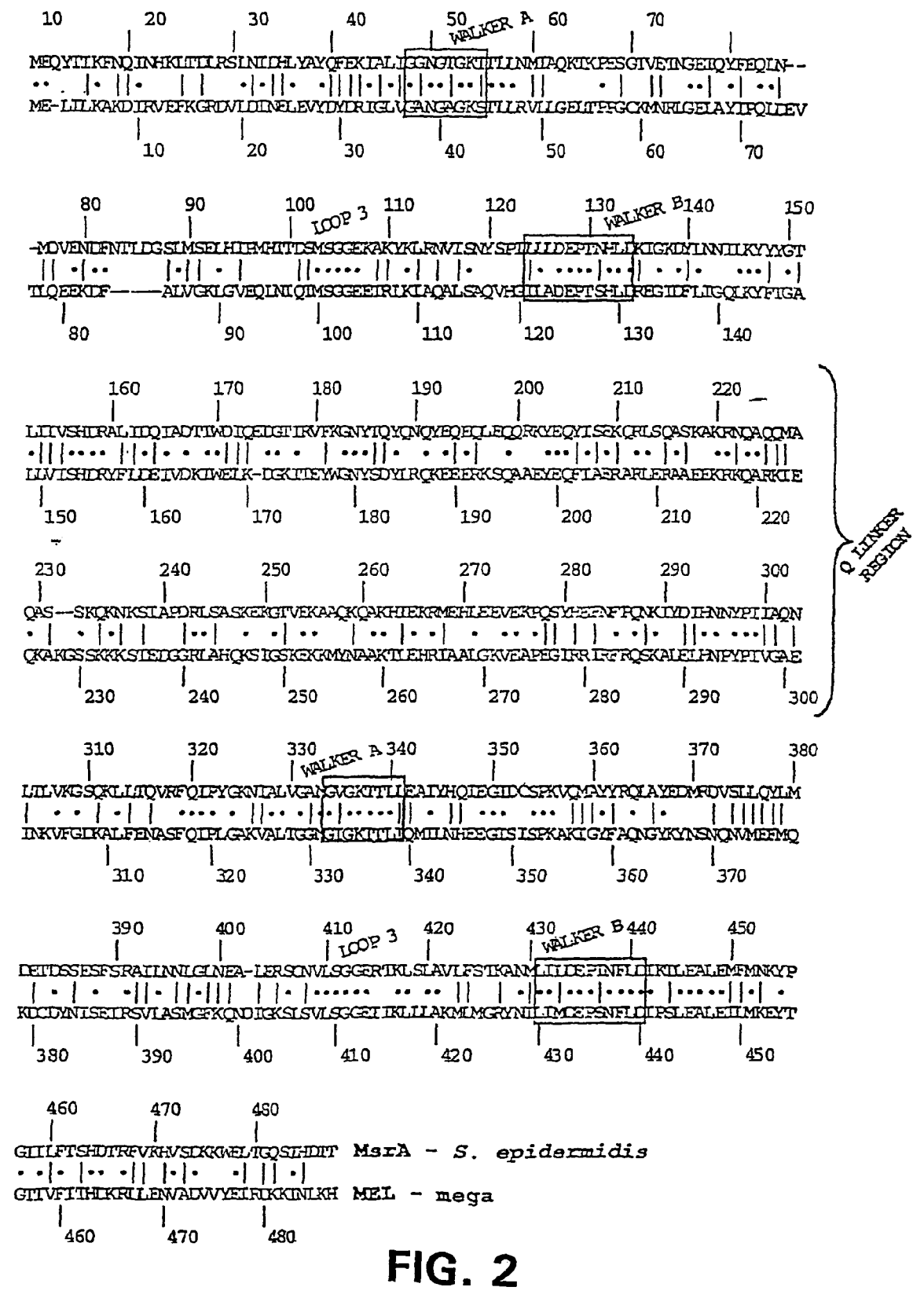
Figure 3:
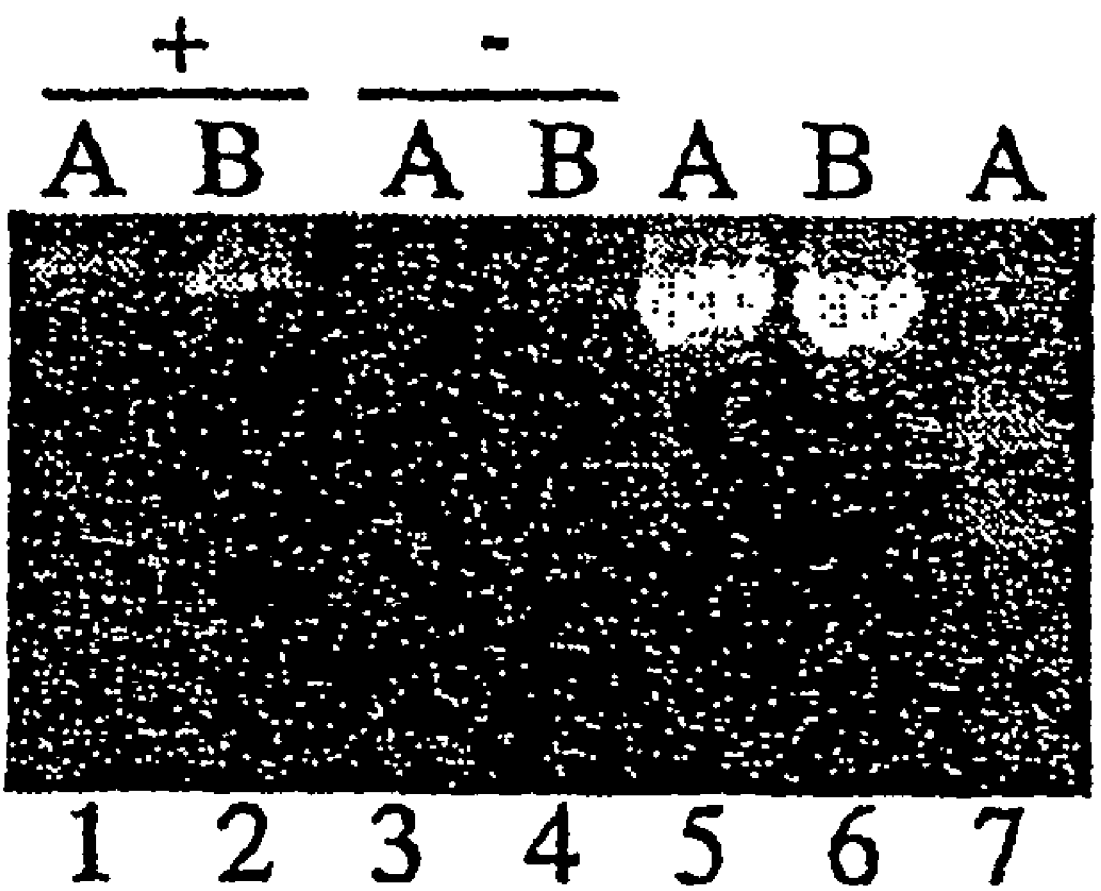
FIG. 3 shows co-transcription of mefE and mel of the mega element. RT-PCR of pneumococcal RNA extracted from strains GA3488 (A) and GA2551 (B). Bacterial RNA was purified from log phase liquid cultures, and RT-PCR was performed as described herein below. Briefly, cDNA was generated with the mef-specific forward primer, KG5F. mef-mel PCR products were amplified using KG5F and the mel-specific reverse primer, KG18R. The samples were analyzed by electrophoresis in a 1.5% agarose gel stained, with ethidium bromide. Reactions were performed with reverse transcriptase (lanes 1 and 2) or without reverse transcriptase (lanes 3 and 4). Lanes 5 and 6: DNA controls. Lane 7: total RNA from GA3488.

The sequence immediately 3' of mefE contained a 1464 bp ORF with the same orientation and was designated mel for the one-letter symbols of the first 3 amino acids. The protein encoded by this ORF showed 36.2% amino acid identity to the erythromycin resistance ATP-binding protein MsrA (SEQ ID NO:7) of *Staphylococcus epidermidis* (SWISS-PROT accession no. P23212, FIG. 2). Between mefE and mel in GA3488 was a 119 bp intergenic region. This 119 bp region contained a consensus Shine-Dalgarno sequence upstream from the predicted start codon for mel. RT-PCR demonstrated that mefE and mel were co-transcribed (FIG. 3).

3' from mel, at nucleotide positions 4044 to 4342 and 4329 to 4641 were two overlapping ORFs (ORF 3 and ORF 4) which were oriented opposite to mefE and mel. The encoded proteins of these ORFs had 52% and 38% identity to the predicted proteins of ORFs 11 and 12 of Tn5252 of *S. pneumoniae* (GenBank accession no. L29324). The first 4 ORFs of mega and Tn1207.1 ORFs 4, 5, 6 and 7 had greater than 94% identity at the nucleotide level. A fifth ORF, also with a reverse orientation relative to mefE, was located between bp 4711 and 5046 of mega. ORF 5 of mega and ORE 8 of Tn1207.1 had 92% identity at the nucleotide level. Mega's ORF 5 had 59% nucleotide identity with ORF 13 of Tn5252, and 45% with ORF U of a lactococcal plasmid (GenBank accession no. U36837). ORF 5 of mega, ORF 13 of Tn5252 and ORF U of *L. lactis* are predicted homologues of umuC of *E. coli* (FIG. 4) [28,29]. However, the intergenic region between ORF5 and ORF4 of mega were different from Tn5252 and Tn1207.1. Associated with ORF5 (beginning at position 5449) was a 20 bp segment homologous with the *E. coli* LexA binding site [30]. Approximately 150 bp of the 3' end, including the Lex A binding sequence, were unique to mega The 5' and 3' ends of the mega element had imperfect inverted terminal repeats that were also unique (FIG. 1).

Mega insertion sites were determined (FIG. 5). The pneumococcal nucleotide sequences adjacent to the terminal inverted repeats of mega in isolate GA3488 (serotype 6A) were 92.5% homologous (817/883 bp identity) with the TIGR *S. pneumoniae* Contig. SP-66. The 5.5 kb mega element had inserted into an ORF predicted to encode a homologue of the phosphomethyl pyrimidine kinase of *Bacillus subtilis* in an orientation opposite to the chromosomal ORF. Mega in this genomic location was designated as a Class I mega insert. The amino acid sequences of the protein encoded by ORF5 of mega is given in SEQ ID NO:6, and the genomic sequences flanking the four mega insertions analyzed are given in SEQ ID Nos:11-16. See also the description of FIG. 5.

A second insertion site for mega was defined in pneumococcal isolate GA2551 (serotype 14). The second site was located in the TIGR *S. pneumoniae* Contig. SP-101 at bp 1003. The sequence flanking the mega insert in GA2551 showed 91.8% nucleotide homology (460/501 bp identity) with this TIGR *S. pneumoniae* sequence. At this location, a 5433 bp mega insert was found disrupting an ORF predicted to encode a homologue of the DNA-3-methyladenine glycosidase of *Haemophilus influenzae*. This second site of mega insertion, designated Class II, was also oriented in a direction opposite to the chromosomal ORF. The nucleotide sequence of the 5.4 kb Class II mega element was identical, except for a 99 bp deletion in the region between mefE and mel which eliminated the consensus Shine-Dalgamo sequence upstream from the mel predicted start codon.

Two additional mefE-containing clinical isolates GA4175 (serotype 19A) and GA4375 (serotype 19F) that did not have Class I or II mega insertions were located in distinct sites (insertion sites Class III and IV). The 260 bp sequence 5' of mega in the Class III insert site showed 93% identity to the nucleotide sequence in Contig SP-15 of the pneumococcal genome. The mega element was found in the same orientation as an ORF predicted to encode a protein with homology to Cap5D of *S. aureus*. In the Class IV insert site, mega had inserted in the pneumococcal genome at contig SP-28 at nt 1329. Mega was in the same orientation as an ORF predicted to encode a protein with homology to an RNA-methyltransferase of *B. subtilis*. The intergenic region between ORFs 1 and 2, in the Class I and II mega elements consisted of 119 nucleotides. In the Class II and IV mega alleles, the region was truncated by 99 bases.

The 5' and 3' ends of the four different mega insertions and the pneumococcal genomic sequences immediately adjacent were compared (FIG. 5). Mega had identical seven base pair imperfect inverted repeats at the ends of each insertion. The *S. pneumoniae* genomic nucleotides immediately adjacent to mega in the four insertion sites were related.

The breakdown of mefE insert location types within the population was studied. PCR primers specific to the pneumococcal genomic sequences flanking the insert sites were used to screen 89 mefE-positive invasive isolates. Primers defined a 6100 bp product in class 1 inserts. This PCR product was detected in 15.7% (14/89) of the mefE-positive strains. Ten of the fourteen isolates containing the class 1 insert were serotype 6A, one was serotype 19A, one serotype 14, and one was not typable. The sequences of the insertion sites of two additional class 1 inserts, GA2401 and GA5056, which are serotypes 6A and 19A, respectively, were confirmed to be identical to that of GA3488. All contained the 5.5 kb mega insert.

Screening of the 89 isolates with primers specific to chromosomal sequence flanking the class 2 insert produced an expected 6 kb fragment in 62% (42/89) of the mefE-positive invasive isolates. Of isolates containing class 2 inserts, 43.5%, 26.7%, and 13.0% were serotype 14, 6B and 6A, respectively and 17.4% were not typable. The class 2 insertion site nucleotide sequences and mega termini of 4 of the serotype 14 strains were identical, as was the 19A isolate. All class 2 inserts contained the 5.4 kb-size mega element. Fifteen percent of the 89 isolates contained wild-type sequences at the class 1 and class 2 locus, confirming the additional sites of mega insertion.

Our studies indicate that mefE has rapidly disseminated and is now responsible for over 75% of erythromycin resistance in S. pneumoniae in metropolitan Atlanta. The mefE gene is a component of a unique 5.5 or 5.4 kb genetic element designated mega. Two putative macrolide efflux pumps of different classes are located in tandem within the element, suggesting coordinate regulation. The three other open reading frames share homology with ORFs of the Tn5252 and are arranged in a convergent orientation to mefE and mel. The ORFs may be important for element movement and may involve a SOS stress response through a LexA-like repressor. The element does not contain a recognized transposase or integrase. Mega has terminal inverted repeats, which are not duplicated, and the element has inserted in at least four specific sites within the pneumococcal genome. Preliminary analysis of the population-based collection of pneumococcal isolates suggests the mega element is now disseminating in S. pneumoniae by transformation and clonal expansion.

The range of MICs for pneumococci containing mega is 1-32 µg/ml. This range may be due to differences in the expression of mefE and mel and/or the substrate specificity of these putative dual efflux pumps. Strain differences may also contribute to this range.

Mega confers macrolide resistance in S. pneumoniae. To show that mega confers M phenotype macrolide resistance in S. pneumoniae, a 6.3 kb PCR product composed of mega and 747 bp of flanking DNA was amplified from the Class I insert in GA3488. This PCR fragment was transformed into the erythromycin sensitive (mefE-) strain R6. Erythromycin-resistant transformants were obtained at a frequency of approximately $2\times10^{-4}$ µg/DNA. The control parent strain, R6, grew only on non-selective plates. The Class I chromosomal location of mega in the transformants was confirmed by PCR and nucleotide sequencing.

Mega insertions in the S. pneumoniae population were studied. The population-based collection of mefE-containing invasive S. pneumoniae isolates from Atlanta was used to study mega insertions within individual pneumococcal isolates (Table 2). PCR primers specific to the sequences flanking the Class I-IV mega insert sites were used to define the location of mega and adjacent DNA in 89 mefE-containing invasive pneumococcal strains isolated in Atlanta from 1994-1996. A Class I product was detected in 15.7% (14/89) of the mefE-positive strains. The nucleotide sequences of the termini of the element and adjacent DNA in four Class I inserts, three serotype 6A and one serotype 19A, were confirmed to be identical to those of GA3488. All Class I inserts contained the approximately 5.5 kb mega element.

Class II mega inserts were found in 62% (55/89) of the mefE-containing invasive isolates. The 5.4 kb mega allele was present in each of the Class II strains. The nucleotide sequences of the Class II insertion sites and mega termini of seven of the serotype 14 strains were sequenced and found to be identical to the prototype strain GA2551 (serotype 14), as were two serotype 6B isolates. In the 20/89 isolates not having Class I or Class II mega inserts, three were Class III, one was a Class IV and 16 contained mefE of undefined insert types.

Figure 6:
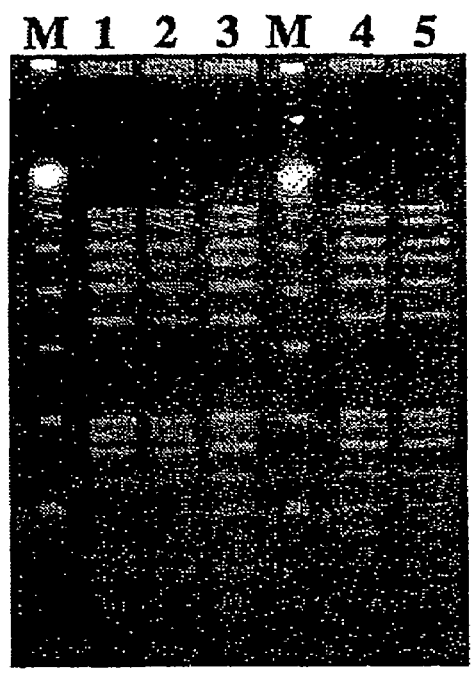
FIG. 6 shows the results of PFGE of mega insert Class II showing closely related (lanes 1 and 2) and identical isolates (clones), (lanes 3, 4 and 5). M, 50 kb 1 ladder; lanes 1-5, strains GA5196, GA4313, GA4988, GA2092 and GA2551.
Figure 7:
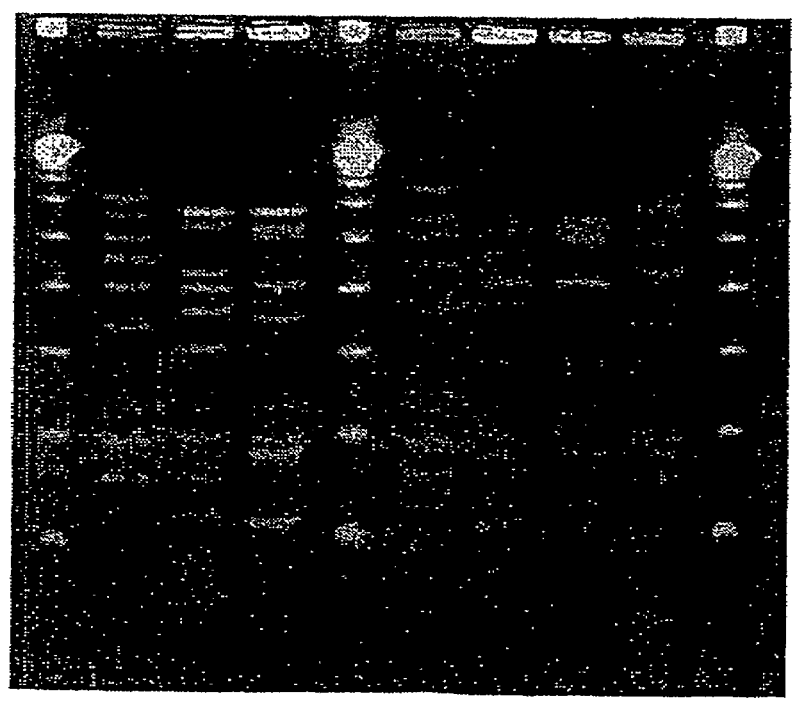
FIG. 7 shows the results of PFGE of mega insert Class II showing possibly related (lanes 5 and 6) and unrelated isolates (lanes 1, 2, 3, 4 and 7). M, 50 kb 1 ladder; lanes 1-7, strains GA2566, GA4672, GA2572, GA2073, GA4796, GA5248 and GA2551.

Pulsed-field gel analysis (PFGE) of 56 of the 89 mega-containing isolates showed 19 distinct PFGE types. Isolates were related (e.g., having PFGE band differences=3 [McDougal et al. *Antimicrob. Agents Chemother.* (1998) 42:2312-2318], an identical location and size of the mega insertion, and identical nucleotide sequence adjacent to the insert) or were unrelated by PFGE. As an example, five serotype 14 isolates recovered between Jan. 1, 1994 and Jul. 2, 1995 from epidemiologically distinct patients in metropolitan Atlanta were indistinguishable or closely related by PFGE (FIG. 6). These isolates contained the 5.4 kb mega allele in a Class II insertion site. The pneumococcal chromosomal sequence adjacent to the Class II mega insert was indistinguishable in all of these isolates. In contrast, other serotype 14 isolates containing the Class II mega insert were unrelated by PFGE, although the genomic location and size of the mega insert and adjacent nucleotide sequence were indistinguishable (FIG. 7). Similar results were seen with other serotypes. These data indicate that mega is spread in S. pneumoniae by clonal expansion and horizontal transfer.

Macrolide resistance associated with mefE has rapidly emerged in S. pneumoniae. We found that mefE is part of a new genetic insertion element responsible for the emergence of rapidly disseminated macrolide resistance in S. pneumoniae in North America. This element contains an operon with two ORFs, mefE and mel. The three other ORFs (ORFs 3, 4, 5) of mega share homology with ORFs 11-13 of Tn5252 and are convergent to mef and mel. The functions of these ORFs are unknown, but recent evidence suggests ORF 13 of Tn5252 is involved in the SOS response in pneumococci [29]. Two other potential regulatory components of mega, a LexA binding domain in ORF5 and a cin box within mefE further suggest that this element may be regulated by competence and SOS stress response events [32,33]. Mega has imperfect terminal inverted repeats that are not duplicated at the site of insertion and the element is found in at least four distinct sites within the pneumococcal genome.

Mega contains an operon potentially encoding two distinct classes of efflux pumps. The first ORF in this operon, mefE, shares ~90% homology with mefA at the nucleic acid level [12]. mefA of *Streptococcus pyogenes* encodes a protein with twelve membrane-spanning regions that can be divided into two domains similar to those of the tetracycline protein motive force transporters found in gram-negative bacteria [10]. Experimental evidence supporting a proton motive function of MefE was demonstrated by a decrease in the efflux of [$^{14}$C]-erythromycin in the presence of proton motive pump inhibitors carbonylcyanide-m-chlorophenylhydrazone (CCCP) and arsenate [9,10]. A 3.7 kb fragment of pneumococcal DNA containing the 1.2 kb mefE gene, was reported to be sufficient for conferring erythromycin resistance when cloned into susceptible strains of *E. coli* strains [34], but the additional DNA contained in the fragment was not characterized. We demonstrate that mega confers macrolide resistance when transformed into S. pneumoniae.

The second ORF of the efflux operon, mel, is a homologue of msrA which encodes an ATP-binding cassette (ABC) that provides the energy for macrolide and streptogramin B efflux in staphylococci [35]. The 1.46 kb msrA gene of *Staphylococcus epidermidis* confers active [$^{14}$C]-erythromycin efflux when cloned into S. aureus [36]. MsrA interacts with as yet unidentified transmembrane proteins to allow erythromycin efflux [36]. The deduced 488 amino acids of MsrA have motifs common to the ABCs of gram-negative bacteria and eukaryotes [37]. Each of the two ABC transporter domains consists of two ATP-binding motifs [38]. Between these ATP-binding motifs lies a highly conserved SGG protein sequence which forms loop 3 of the predicted tertiary structure and is predicted to interact with the cell membrane [39]. MsrA is the prototype of a subfamily of ABCs that are characterized by an interdomain "Q-linker" [39,40]. The position of mefE and mel in the mega element and their co-transcription as an operon suggest that the encoded proteins are a dual efflux system in S. pneumoniae. Increasing MICs of mef-containing isolates to macrolides have been noted by us [13] and others. The role of the MsrA homologue encoded by mel in macrolide-resistance is unknown, but may contribute to higher levels of macrolide resistance.

The amino acid sequence homology between ORF5, ORF4 and ORF3 of mega and ORF11, 12 and 13 in Tn5252 suggest that mega is related to conjugative transposons. Conjugative transposons (e.g., Tn5252) insert by a non-duplicative, site-specific recombination mechanism similar to that of bacteriophages. Although mega lacks enzymes required for such DNA transposition, the similar insertion site sequence, the nonduplicative insertions and evidence of carry over bases suggest mega was initially introduced into the pneumococcal chromosome by a site-specific event. In support of this hypothesis, a related genetic element (Tn1207.1) was recently described by Santagati et al. [14]. Tn1207.1 is a 7244 bp defective transposon containing mefA and four downstream ORFs with similar homology and position as the corresponding ORFs of mega. However, we did not detect a mefE(A)-containing element of this size in any of the pneumococcal isolates we studied, and the sequence 5' of mefA in Tn1207.1 contains three additional ORFs with recombinase and integrase homologies. Further, the 944 bp and 150 bp 5' and 3' termini, including the LexA binding sequence, are unique to mega. Also, the insertion site of the mefA-containing Tn1207.1 is a transformation-specific locus of the pneumococcal chromosome [14] that we have not found as a mega insertion site.

Mega may be influenced by competence and SOS stress events. ORF13 of Tn5252 and ORF5 of mega have homology to UmuC. In Tn5252, ORF13 is followed by ORF14, an UmuD homologue. The UmuC and D homologues of Tn5252 restore error-prone repair in S. pneumoniae [29], and the expression of the Tn5252 umuCD operon is regulated by the RecA and LexA proteins. Although an UmuD homologue is absent in mega, ORF5, the mega UmuC homologue has a consensus LexA binding sequence. In addition to ORFs 3,4 and 5, the complement of the strand encoding mefE contains a TACGAATA sequence. Campbell et al. postulate that this sequence is part of a core promoter consensus recognized by an alternative sigma factor critical for the expression of competence-induced elements [32]. This sequence, which Claverys and Martin [41] refer to as a "cin box", is found in nine putative competence loci of the pneumococcal genome.

The dissemination of mega in S. pneumoniae was studied in pneumococcal isolates obtained from a defined human population undergoing active population-based surveillance for S. pneumoniae invasive disease. In six years of surveillance (1994-1999), rapid increases in macrolide resistance rates were linked with mega [13]. In this study, we show identical mega insertions and adjacent chromosomal DNA in epidemiologically and genetically unrelated pneumococcal strains obtained from the surveillance. These data indicate that transformation and homologous recombination have spread mega in S. pneumoniae. Serotype data from our six-year surveillance showing the appearance of mega in new serotypes [13], and experimentally by transformation of mega and induction of macrolide resistance in susceptible S. pneumoniae provide further support.

Evidence for dissemination of mega by clonal expansion was also found in this study. Serotype 14 isolates identical by PFGE, mega insertion and adjacent DNA were recovered from geographically and temporally unrelated pneumococcal isolates in metropolitan Atlanta. Spread of drug-resistant pneumococcal clones has been previously documented for serotypes 23 and 14 [42,43]. The pressure of increased macrolide use appears to select for the clonal expansion of pneumococci that harbor mega and for transformation events spreading mega to other pneumococcal strains.

In summary, S. pneumoniae in our population are rapidly developing resistance to macrolide antibiotics due to the dissemination of the novel 5.5 or 5.4 kb genetic element mega. The element contains genes that may encode two distinct classes of efflux pumps. Mega has features of a defective conjugative transposon. Without wishing to be bound by any particular theory, it is believed that mega influences or is influenced by the competence and SOS systems of streptococci. Mega appears to have entered the pneumococcal genome on at least four occasions by site-specific recombination events, but has rapidly expanded in the pneumococcal population by the selection of mega-containing clones and has spread horizontally by transformation. The emergence of mega in S. pneumoniae demonstrates how rapidly selection of a genetic element can occur in vivo in this important human pathogen, and urges the judicious use of antibiotics.

RT-PCR and primer extensions are used to assess co-transcription and define the promoter(s) of mefE and mel. The promoter(s) is mapped, analyzed and compared to other prokaryotic promoters in the databases. Factors that influence the mefE and mel promoter(s) is then identified using a lacZ reporter-gene construct. The effects of a sequential series of deletions in the promoter region are studied using this reporter system. Without wishing to be bound by any particular theory, we believe that environmental conditions, e.g., the expression of competence-stimulating peptide (CSP) during exponential growth, sub-MIC macrolide and streptogramin B concentrations influence mefE/mel expression.

RT-PCR is performed using GeneAmp® (Perkin Elmer, Branchburg, N.J.). RNA is prepared from pneumococcal strain GA3488 (serotype 6A; class 1, 5.5 kb mega insert) and GA2551 (serotype 14; class 2, 5.4 kb mega insert). These two strains were chosen to assess the importance of the 99 bp difference between mefE-mel in mega allelic forms. The RNAs serve as templates for the reverse transcription of cDNA templates. Three PCR primers sets are used to define 346 and 520 bp regions internal to mefE and mel, respectively, and 2180 bp or 2081 bp of a transcript spanning these two ORFs. RNA without reverse transcriptase serves as a control.

To define the promoters of mefE/mel, the AMV Reverse Transcriptase Primer Extension System (Promega, Madison, Wis.) is used as previously described [Swartley et al. J. Bacteriol. 1998. 180: 1533-1539]. The transcriptional start site identified is used to define the promoter, including −10 and −35 regions and other possible cis regulatory features (e.g., palindromes, regulatory sequences, IHF binding sites). See also FIG. 1, inset.

To identify factors that influence mefE/mel transcription, a plasmid containing a mefE promoter::lacZ gene fusion, pKG2, is constructed. A 1973 bp PCR product defining, the entire 5' portion of mega and the first 401 bp of mefE, is cloned into pGEM-T® (Promega, Madison, Wis.) to create pKG1. The EcoRI fragment of pAErmC'G containing a lacZ cassette is inserted into the unique MunI site, 14 bp downstream from the mefE start codon, to create pKG2. Plasmids are maintained in the *E. coli* DH5α. Blue colonies indicating lacZ expression by the mefE promoter are selected from plates containing 500 μg/ml Xgal. Clones containing the lacZ cassette in both orientations are confirmed by PCR and sequencing. The lacZ cassette in the reverse orientation serves as a negative control. Pneumococcal strain GA3488 is transformed with pKG2 [Yother et al. *J. Bacteriol.* (1986) 168:1463-1465]. Transformants, in which the wild type mefE is replaced by the lacZ transcriptional reporter, are selected by screening for Ery$^S$ colonies using a replicative plating method. Transcriptional fusions are evaluated for β-galactosidase activity [Miller, 1972, vide infra]. Deletions within the putative mefE promoter of pKG2 are generated with Erase-a-Base® (Promega) to further characterize the putative promoter. This system takes advantage of the uniform rate of 5' overhang digestion by ExoIII to create a sequential series of deletions. The BsmI site located 212 bp upstream from the ATG start site of mefE provides such a site. S1 nuclease is then added to create a blunt end for ligation purposes. Plasmid DNAs is transformed into GA3488 as described above.

To determine whether growth conditions play a role in mefE and mel regulation, mel expression during a standard growth curve in Todd-Hewitt broth supplemented with 0.5% yeast extract. Media pH affects competence [Bricker et al. *FEMS Microbiol. Lett.* (1999) 172:131-135]. Expression of mefE/mel in media whose pH ranges from 6.8 to 8.0 is determined. Increases in [$Ca^{2+}$] to 1 mM also triggers competence for genetic transformation during exponential growth [Trombe et al. *J. Gen. Microbiol.* (1992) 138:77-84]. Possible effects on mefE/mel transcription by divalent cations are investigated by altering the [$Ca^{2+}$] from 0.15 mM which is required for optimal growth. Expression of mefE/mel during growth at temperatures ranging from 25° C. to 42° C. is also assessed.

To define the effects of various efflux pump substrates on mefE/mel reporter gene expression, sub-MIC levels of macrolides of different classes, other antibiotics (e.g., streptogramins), dyes (crystal violet) and detergents (Triton X-100) are used once the pump substrates have been identified. To test the role of competence induction in the regulation of mefE/mel we add 100 ng/ml synthetic competence-stimulating peptide (CSP; Chiron Mimotopes) and/or adjust the media pH to 7.2 as described by [Pestova et al. *J. Bacteriol.* (1998) 189:2701-2710]. Competence is suppressed by growing cells under acidic conditions. The expression of mefE/mel in RecA-, mega ORF5- and LexA binding site altered mutants is determined.

MefE is reported as a single component efflux pump. However, the genetic organization and homology data suggest both mefE and mel gene products are involved in macrolide efflux. Whether both gene products influence the range of MICs to macrolides and whether the efflux of other hydrophobic agents, dyes and detergents is a function of these gene products are determined.

In the characterization of the mel homologue, msrA, Ross et al. [35] found that MsrA had two ATP binding motifs and appeared to function independently when cloned in a heterologous host. However, MsrA did not contain transmembrane binding domains characteristic of fused ABC transporters, suggesting a relationship with other membrane proteins. MefE has previously been described as conferring a macrolide-only resistance phenotype. Based on the homology to MsrA, and without wishing to be bound by theory, Mel is believed to transport both streptogramin B and macrolides.

Polar and nonpolar mutations in mefE and mel or both are created in strain GA3488: a polar mefE mutant, a polar mel mutant, a polar mefE/mel double knockout mutant and a nonpolar mefE mutant. A 3115 bp PCR product defined by primers KG11 and KG29R containing mefE, mel and 273 bps upstream of mefE is cloned into the pGEM-T® vector. A 602 bp deletion in mel is created by digestion with EcoRI. This site is used for inserting a 2076 bp (Ω) spectinomycin resistance (Spec) cassette obtained from pHP45ΩSimilarly, a 661 bp fragment of mefE is deleted using Csp451 and DraII for the introduction of a Spec cassette. A Spec cassette is also used to select a third construct generated by removing a 2136 nucleotide region spanning both ORFs with HpaI and DraII. The aphA-3 nonpolar cassette [Menard et al. *J. Bacteriol.* (1993) 175:5899-5906] is inserted into mefE after introducing NcoI and SpeI sites into this ORF by PCR. These constructs are maintained in *E. coli* DH5α, and transformed into the parent strain, GA3488, as described by Yother et al. *J. Bacteriol.* (1986) 168:1463-1465. Following selection on Todd-Hewitt agar plates containing spectinomycin and kanamycin, single colonies are confirmed by PCR and sequencing. A second strategy for creating mef and mel deletions can be accomplished by PCR.

Sutcliffe et al. previously provided evidence that mefE was inhibited by uncouplers of electrochemical proton gradients such as carbonyl cyanide-m-chlorophenylhydrazone (CCCP). However, these experiments did not determine if reenergization of the membrane with glucose can reverse the effect of CCCP, an important requirement for confirming proton motive force pumps. The accumulation of $^{14}$C-erythromycin or [$^3$H]-TX-100 as described by Sutcliffe et al. and Lucas et al. for the Ω spec and aphA mutations in mefE and mel is determined [Sutcliffe et al. *Antimicrob. Agents Chemother.* (1996) 40:1817-1824; Lucas et al. *Molec. Microbiol.* (1996) 16:1001-1009]. In addition minimal inhibitory concentrations (MICs) for erythromycin, azithromycin, clarithromycin, streptogramins, crystal violet and TX-100, will be determined by broth dilution method in the wild type and in the four mefE and mel polar and nonpolar mutants. Antibiotics(e.g., spectinomycin and penicillin) not dependent upon efflux pumps are used as controls to assess nonspecific membrane changes.

The allelic form of mega typified by strain GA3488 contains a Shine-Dalgarno sequence upstream of the mel ATG codon. This site is absent in the mega of strain GA2551 since it occurs at the end of the variable 99 bp intergenic region. This streptogramin resistance is observed in strains such as GA3488 whereas others lacking a Shine-Dalgarno sequence upstream of mel, e.g., GA2551 are streptogramin sensitive. A preliminary screening of the 1998 invasive pneumococcal isolates revealed that approximately half were resistant to quinupristin, a streptogramin B analogue. All 1998 and 1999 pneumococcal isolates are screened for the presence or absence of the variable 99 bp mefE/mel intergenic region by PCR using primers KG8 and KG10 which define a 554 or 455 bp sequence depending on the allelic form. The results are compared with quinupristin sensitivity data. These data are confirmed by the introduction of the mef/mel mutations into strain GA2551.

mefE and mel are co-transcribed on the same mRNA message. A single start site as defined by primer extension is located upstream of mefE. While a separate promoter region for mel may be located at the 3' end of mefE, this appears to be unlikely since the mefE-mel intergenic region can vary by 99 bp, and mel appears to lack a typical independent promoter region. Thus, a single reporter in mefE is used to answer whether the transcription of mefE and mel are constitutive and regulated by growth, substrate or environmental conditions such as competence induction.

Gene reporter experiments must utilize negative controls, and one must consider the background of the strain to be used. Controls include strain GA3488 alone, the plasmid vector without the promoter region and the lacZ cassette in the reverse orientation. Endogenous lacZ activity could be present in GA3488. GA3488 lacZ-mutants could be selected by a method described by Pearce et al. (1995) supra. Alternative approaches include transforming a lacZ-strain R6 derivative with a construct consisting of a mefE promoter::lacZ gene fusion flanked by nonessential chromosomal DNA of the class I site, or transformation of this class 1 mefE promoter::lacZ gene fusion into pneumococcal strain GA2551 which has an intact class 2 mega element.

Constructs containing an intact mefE display an increase in $^{14}C$-erythromycin accumulation in the presence of CCCP, which can be rescued by glucose. This effect is more pronounced in strains which also lack a functional mel.

Without wishing to be bound by any particular theory, Mega is believed to be a defective (hitchhiker) transposable element. Mega affects and is affected by transformation/competence and the pneumococcal SOS network. The genetic structure of the mega element, in particular ORFs 3-5, supports this view.

It is believed that the initial introductions of mega into the S. pneumoniae genome were the result of an illegitimate site-specific recombination mechanism. Transposition of mega in S. pneumoniae requires additional enzymes expressed in trans by Tn5252 or other conjugative transposons and may require ORFs 3-5. ORFs 3-5 appear to form an operon that may influence transposition or horizontal transfer via transformation.

The position and orientation of ORFs 3, 4 and 5 indicate they are transcribed as an operon. ORFs 3, 4 and 5 of mega share 52%, 38% and 59% nucleotide identity and similar locations with ORFs 11, 12 and 13, of Tn5252. ORFs 11-13 in Tn5252 are proposed as part of an operon that may provide UmuCD homologues to S. pneumoniae for error-prone DNA repair.

RT-PCR and b) primer extensions are used to assess co-transcription and the promoter(s) of ORFs 3, 4 and 5. The promoter(s) are mapped and compared to other prokaryotic promoters in the database. Briefly, RT-PCR is performed to address the question of whether ORF4 is part of an operon with ORF5 or is independently transcribed. Following the isolation of RNA from strain GA3488, a cDNA template is generate using a primer, KG26R, specific to the 3' end of ORF4. Two PCR primers sets are used to define regions internal to ORF4 and ORF5, or a possible 1 kb transcript spanning these two ORFs. The forward primers, KG24F and KG40 are used with KG26R for this purpose. The AMV Reverse Transcriptase Primer Extension System (Promega, Madison, Wis.) is used as previously described [Swartley et al. 1996. supra].

The similarity between ORFs 3, 4 and 5 of mega and ORFs 11, 12 and 13 of Tn5252 suggests that mega is related to conjugative transposons. The 5' end of Tn5252 encodes the integrase, excisionase, repressor protein and relaxase [Kilic et al. (1994) supra] which are not found in mega. Mega also resembles a transposable element in that the terminal ends consists of inverted repeats, and there appears to be a 5 bp carry-over of the class 1 target site which is found at the ends of mega in other insertion sites. This is like Tn916 in which six extra bases, which correspond to those adjacent to the transposon in the previous host, are introduced with the transposon.

Using three methods, we assess whether mega can excise and transpose and whether this requires "helper genes" of conjugative transposons. PCR detection of closed circular transposon intermediates, conjugative mating experiments between resistant donors and susceptible recipients, and the transposition of mega to a plasmid containing cloned, wild type mega insert sites are used. Defined mutations in mega's ORF 3, 4 and 5 are used to assess the possible role of these open reading frames in the transposition of mega.

Conjugative transposons and many other transposable elements excise from their sites of insertion and form closed circular intermediates. These circles are then capable of inserting into a new genomic location, or of being transferred to a new host by conjugation. Many pneumococcal antibiotic resistance determinants are carried on conjugative transposons (i.e. Tn3701-5, Tn1545, Tn5252 and Tn3951). We first assess closed circular intermediates of mega in pneumococci with mega, pneumococci with mega and Tn5252 and pneumococci with mega and other conjugative transposons. Specific oligonucleotide primers, KG12 and KG26, which bind near the ends of mega are used to amplify by PCR a fragment spanning the junction. We have used this procedure previously in Tn916 [Swartley et al. *Molec. Microbiol.* (1993) 10:299-310]. The technique is very sensitive, can be semi-quantitative and provides an indirect measure of the excision of mega in different genetic backgrounds (e.g., strains with or without conjugative transposons). Pneumococcal strains GA2341 and GA4216 obtained from our population-based collection of isolates and other strains containing defined conjugative transposons (see below) are used.

As a second assessment of transposition, pneumococcal strains containing mega and tetM (a marker for conjugative transposons) in different genetic backgrounds (GA2693 and GA4216) are used as donors in filter-mating experiments with *S. pneumoniae* strain R6 (mefE-, tetM-) as the recipient. Mega transposition occurs with the transfer of conjugative transposons. The donor strains contain mega and transposons Tn5252, Tn1545, Tn3872 or other conjugative transposons. Mega is inserted into pneumococcal strains (e.g., BM4200) containing defined conjugative transposons (e.g., Tn1545). Filter mating is conducted in the presence or absence of DNase to help differentiate between transformation and conjugation. Transconjugants are selected for by growth on both erythromycin/tetracycline and erythromycin plates and subsequently screened for mega by PCR. The insertion sites of mega in the transconjugants are determined by PCR using primers specific to the genomic sequence surrounding the mega insertions. The resulting PCR products are sequenced in order to distinguish by genetic polymorphisms between transformation and transposition events. In the event that these primers do not reveal the insertion site, SSP-PCR and sequencing are used to ascertain the location of mega Donor pneumococcal isolates without mega serve as positive controls. The transfer frequency of each mating is calculated as the rate per donor colony forming unit. For example, transposition efficiencies for insertion mutants of Tn5252 are reported to be $>2\times10^{-7}$ per donor [Kilic et al. (1994) supra]. As a third approach, the 30 kb conjugative plasmid pIP501 which contains genes for resistance to chloramphenicol ($Chl^R$) and erythromycin ($Ery^R$) [Scott et al. *Molec. Microbiol.* (1994) 112:1099-1108] are also used as a "trap" to evaluate the transposition of mega. Cloning of mega insert sites into the erythromycin gene of pIP501 produces pIP501-IS (Chl$^R$/Ery$^S$). pIP501-IS is introduced into strain GA3488 by conjugation and maintained by passage on chloramphenicol containing Todd-Hewitt plates. Mobilization of mega into the plasmid borne insertion sites is detected by identifying chloramphenicol/erythromycin resistant transconjugants in filter mating experiments using strain R6 as the recipient. Mega insertions in the transconjugants will confirmed by PCR and DNA sequencing.

To determine the role of ORFs 3-5 in the transposition of mega, specific polar and nonpolar mutations in ORFs 3-5 are created. Polar mutations are made by inserting the $\Omega$Spec cassette from pHP45$\Omega$ into ORFs 3, 4, 5 or in a deleted region spanning all three ORFs to create a triple knockout mutant. The aphA-3 cassette is used to make nonpolar ORF5 and ORF4 mutants. Mutations in ORFs 3-5 are tested with donor backgrounds (defined above) in which mega is shown to transpose.

In S. pneumoniae, the transformation/competence network and the SOS regulon overlap and are linked. RecA appears to be the limiting factor in the competitive processes of recombination, and SOS-related error-prone DNA repair [Rehrauer et al. 1998. supra]. In many bacteria, RecA* induces a SOS-related error-prone DNA repair by inactivating LexA. The potential LexA binding site of ORF5 and the similarity between ORF5 and UmuC homologues indicate that mega ORFs 3-5 are regulated by a LexA-like repressor and by RecA*. Since mega lacks enzymes associated with independently transferable elements but contains sequences implicated in pneumococcal transformation, i.e., an UmuC homologue and a LexA binding motif, mobilization of mega is by RecA regulation.

Transformation efficiencies are determined with a chromosomal marker that encodes streptomycin resistance (Str$^R$) for: a) wild type strain R6, b) R6/M, an R6 derivative containing mega (class 1), c) R6/M/X, derived from R6/M by creating a deletion spanning ORFs 3-5 as described herein. d) R6/M/L, an R6/M derivative containing mutations introduced by PCR in the LexA binding motif of ORF5. (A PCR product in which the 5'CTGT of the motif is deleted is used to transform R6/M.) and e) R6/M/R, a recA$^-$ mutant crated by inserting an aphA-3 nonpolar cassette into the RecA locus of R6/M. (Alternatively, R2091, a RecA-deficient pneumococcal containing a chloramphenicol resistance marker in RecA can be used [Martin et al. (1995) supra])

Cells are grown under conditions which favor the development of competence [Pearce et al. (1995) supra]. Str$^R$ chromosomal DNA is added at 2 µg/ml. DNase I is added after a 30 minute incubation to stop further DNA uptake. Following incubation to allow the expression of the antibiotic resistance gene, serial dilutions are made and transformation efficiency for each strain is determined as described by Cheng et al. [Cheng et al. 1997. *Molec. Microbiol.* 23:683-692].

Similarly, the influence of mega on its own mobility is evaluated in filter mating experiments between R6/Str$^R$ recipients and the following donors: a) R6/M, b) R6/M/X and c) R6/M/L. Filter matings are performed as described by McDougal et al. with the omission of DNase I [Mcdougal et al. *Antimicrob. Agents Chemother*. (1998) 42:2312-2318]. Ery$^R$/Str$^R$ transformants are selected. Transfer frequencies are calculated as the rate per donor CFU. Mega class and location are determined by PCR and confirmed by DNA sequencing.

Pulsed-field gel electrophoresis (PFGE), PCR and nucleotide sequencing are used to define strain genetic relatedness and to classify the mega insert and its location in the genomes of our population-based collection of isolates of S. pneumoniae. The Erm$^R$ (>1 µg/ml) invasive pneumococcal isolates prospectively collected in the 1999-2002 Atlanta active, population-based surveillance are tested using PCR for mefE and the presence of the MEGA element. Where positive, the mega insert site (class 1-4, other) and size (e.g., 5.5 or 5.4 kb) is also determined by PCR. New classes of mega insertions are determined by S SP-PCR and nucleotide sequencing as described. These data enable the classification of the mega-containing isolates by insert location and size of the mega insert.

The molecular epidemiological analysis of mega-containing pneumococcal isolates are accomplished by PFGE and mega gene sequence polymorphism studies. PFGE is performed on isolates to assess genetic relatedness of strains. The SmaI restriction profile of each of the strains by PFGE is used to establish strain relatedness and construct dendrograms using the BioImage electrophoresis analysis system and software package [24]. Once completed and recorded, pulse field gels are Southern transferred and probed with mefE to further confirm genetic relationships between strains.

Specific oligonucleotide primers are used to amplify by PCR and sequence ~400 bp segments of the 5' and 3' termini of mega and adjacent genomic DNA. The unlinked housekeeping gene recA is used as a control for gene sequence polymorphism studies. The PCR products of the mega termini contain ~200 bp of pneumococcal genomic DNA and 200 bp of mega The PCR products are purified and sequenced using an ABI Model 377 Automated DNA Sequencer. These studies are designed to assess polymorphisms in the mega termini and in the genomic sites of insertion. Such polymorphisms help determine the relationship of isolates and whether the dissemination of mega is due to homologous recombination or site-specific transposition. Nucleotide sequences from defined gene segments obtained from individual pneumococcal isolates are compared and grouped based A subinhibitory concentration of a compound (such as an antibiotic) is a concentration which does not cause detectable inhibition of growth of a bacterium. Growth can be measured as colony formation on solid medium, as increase in optical density in a liquid culture or as a lawn of growth on a solid medium. Inhibition can be monitored as a reduction in the ability to form colonies from single cells, reduction in growth rate or end point of growth in liquid medium or reduced density of a lawn of bacteria on solid medium (zone of inhibition).

A protein is considered an isolated protein if it is a protein isolated from a host cell in which it is recombinantly produced. It can be purified or it can simply be free of other proteins and biological materials with which it is associated in nature.

An isolated nucleic acid is a nucleic acid the structure of which is not identical to that of any naturally occurring nucleic acid. The term therefore covers, for example, a DNA which has the sequence of part of a naturally occurring genomic DNA molecule but is not flanked by both of the coding or noncoding sequences that flank that part of the molecule in the genome of the organism in which it naturally occurs; a nucleic acid incorporated into a vector or into the genomic DNA of a prokaryote or eukaryote in a manner such that the resulting molecule is not identical to any naturally occurring vector or genomic DNA; a separate molecule such as a cDNA, a genomic fragment, a fragment produced by polymerase chain reaction (PCR), or a restriction fragment;

and a recombinant nucleotide sequence that is part of a hybrid gene, i.e., a gene encoding a fusion protein. Specifically excluded from this definition are nucleic acids present in mixtures of DNA molecules, transformed or transfected cells, and cell clones, e.g., as these occur in a DNA library such as a cDNA or genomic DNA library.

As used herein expression directed by a particular sequence is the transcription of an associated downstream sequence. If appropriate and desired for the associated sequence, there the term expression also encompasses translation (protein synthesis) of the transcribed RNA. When expression of a sequence of interest is "up-regulated," the expression is increased.

In the present context, a promoter is a DNA region which includes sequences sufficient to cause transcription of an associated (downstream) sequence. The promoter may be regulated, i.e., not constitutively acting to cause transcription of the associated sequence. If inducible, there are sequences present which mediate regulation of expression so that the associated sequence is transcribed only when an inducer molecule is present in the medium in or on which the organism is cultivated. In the present context, a transcription regulatory sequence includes a promoter sequence and the cis-active sequences necessary for regulated expression of an associated sequence in response to environmental signals.

One DNA portion or sequence is downstream of a second DNA portion or sequence when it is located 3' of the second sequence. One DNA portion or sequence is upstream of a second DNA portion or sequence when it is located 5' of that sequence.

One DNA molecule or sequence and another are heterologous to another if the two are not derived from the same ultimate natural source. The sequences may be natural sequences, or at least one sequence can be designed by man, as in the case of a multiple cloning site region. The two sequences can be derived from two different species or one sequence can be produced by chemical synthesis provided that the nucleotide sequence of the synthesized portion was not derived from the same organism as the other sequence.

An isolated or substantially pure nucleic acid molecule or polynucleotide is a polynucleotide which is substantially separated from other polynucleotide sequences which naturally accompany a native mega sequence. The term embraces a polynucleotide sequence which has been removed from its naturally occurring environment, and includes recombinant or cloned DNA isolates, chemically synthesized analogues and analogues biologically synthesized by heterologous systems.

A polynucleotide is said to encode a polypeptide if, in its native state or when manipulated by methods known to those skilled in the art, it can be transcribed and/or translated to produce the polypeptide or a fragment thereof. The anti-sense (or complementary) strand of such a polynucleotide is also said to encode the sequence.

A nucleotide sequence is operably linked when it is placed into a functional relationship with another nucleotide sequence. For instance, a promoter is operably linked to a coding sequence if the promoter effects its transcription or expression. Generally, operably linked means that the sequences being linked are contiguous and, where necessary to join two protein coding regions, contiguous and in reading frame. However, it is well known that certain genetic elements, such as enhancers, may be operably linked even at a distance, i.e., even if not contiguous.

The term recombinant polynucleotide refers to a polynucleotide which is made by the combination of two otherwise separated segments of sequence accomplished by the artificial manipulation of isolated segments of polynucleotides by genetic engineering techniques or by chemical synthesis. In so doing one may join together polynucleotide segments of desired functions to generate a desired combination of functions.

Polynucleotide probes include an isolated polynucleotide attached to a label or reporter molecule and may be used to identify and isolate related sequences, for example, those from species of *Streptococcus*, including by not limited to, *S. pyogenes*, *S. pneumoniae*, and *S. agalactiae*. from *Staphylococcus* species including *aureus* and *epidermidis*, *Enterococcus* species, e.g. *Faecium* and *faecalis*. Probes comprising synthetic oligonucleotides or other polynucleotides may be derived from naturally occurring or recombinant single or double stranded nucleic acids or be chemically synthesized. Polynucleotide probes may be labeled by any of the methods known in the art, e.g., random hexamer labeling, nick translation, or the Klenow fill-in reaction.

Large amounts of the polynucleotides may be produced by replication in a suitable host cell. Natural or synthetic DNA fragments coding for a protein of interest are incorporated into recombinant polynucleotide constructs, typically DNA constructs, capable of introduction into and replication in a prokaryotic or eukaryotic cell, especially *E. coli*. Usually the construct is suitable for replication in a unicellular host, such as a bacterium, but a multicellular eukaryotic host may also be appropriate, with or without integration within the genome of the host cell. Commonly used prokaryotic hosts include strains of *Escherichia coli*, although other prokaryotes, such as *Bacillus subtilis* or a pseudomonad, may also be used. Eukaryotic host cells include yeast, filamentous fungi, plant, insect, amphibian and avian species. Such factors as ease of manipulation, degree and control of protein expression, ease of purification of expressed proteins away from cellular contaminants or other factors influence the choice of the host cell.

The polynucleotides may also be produced by chemical synthesis, e.g., by the phosphoramidite method described by Beaucage and Caruthers (1981) *Tetra. Letts.* 22:1859-1862 or the triester method according to Matteuci et al. (1981) *J. Am. Chem. Soc.*, 103:3185, and may be performed on commercial automated oligonucleotide synthesizers. A double-stranded fragment may be obtained from the single stranded product of chemical synthesis either by synthesizing the complementary strand and annealing the strand together under appropriate conditions or by adding the complementary strand using DNA polymerase with an appropriate primer sequence, as well known to the art.

DNA constructs prepared for introduction into a prokaryotic or eukaryotic host typically comprise a replication system (i.e. vector) recognized by the host, including the intended DNA fragment encoding the desired polypeptide, and preferably also include transcription and translational initiation regulatory sequences operably linked to the polypeptide-encoding segment. Expression systems (expression vectors) typically include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Signal peptides from secreted polypeptides of the same or related species, which allow the protein to cross and/or lodge in cell membranes or be secreted from the cell, may also be included, where appropriate.

An appropriate promoter and other necessary vector sequences are selected so as to be functional in the host.

Examples of workable combinations of cell lines and expression vectors are described in Sambrook et al. (1989) vide infra; Ausubel et al. (Eds.) (1995) *Current Protocols in Molecular Biology*, Greene Publishing and Wiley Interscience, New York; and Metzger et al. (1988) *Nature*, 334:31-36. Many useful vectors for expression in bacteria, yeast, fungal, mammalian, insect, plant or other cells are well known in the art and are obtained such vendors as Stratagene, New England Biolabs, Promega Biotech, and others. In addition, the construct may be joined to an amplifiable gene (e.g., DHFR) so that multiple copies of the gene may be made. For appropriate enhancer and other expression control sequences, see also *Enhancers and Eukaryotic Gene Expression*, Cold Spring Harbor Press, N.Y. (1983). While such expression vectors may replicate autonomously, in the alternative, they may replicate by being inserted into the genome of the host cell.

Expression and cloning vectors likely contain a selectable marker, that is, a gene encoding a protein necessary for the survival or growth of a host cell transformed with the vector. Although such a marker gene may be carried on another polynucleotide sequence co-introduced into the host cell, it is most often contained on the cloning vector. Only those host cells into which the marker gene has been introduced survive and/or grow under selective conditions. Typical selection genes encode proteins that confer resistance to antibiotics or other toxic substances, e.g., ampicillin, neomycin, methotrexate, etc.; complement auxotrophic deficiencies; or supply critical nutrients not available from complex media. The choice of the proper selectable marker depends on the host cell; appropriate markers for different hosts are known in the art.

Recombinant host cells, in the present context, are those which have been genetically modified to contain an isolated DNA molecule of the instant invention. The DNA can be introduced by any means known to the art which is appropriate for the particular type of cell, including without limitation, transformation, conjugation, lipofection, electroporation or transduction.

It is recognized by those skilled in the art that the DNA sequences may vary due to the degeneracy of the genetic code and codon usage. All DNA sequences which code for a Mega protein are included in this invention, including DNA sequences as given in SEQ ID NO:1.

Additionally, it will be recognized by those skilled in the art that allelic variations occur in DNA sequences which do not significantly change activity of the amino acid sequences of the peptides which the DNA sequences encode. All such equivalent DNA sequences, especially synonymous coding sequences, are included within the scope of this invention and the definition of the Mega. The skilled artisan understands that the sequence of the exemplified Mega sequence can be used to identify and isolate additional, nonexemplified nucleotide sequences which are functionally equivalent to the coding and other sequences given in SEQ ID NOs:1-6.

Hybridization procedures are useful for identifying polynucleotides with sufficient homology to the sequences to be useful as taught herein. The particular hybridization techniques is not essential to the subject invention. As improvements are made in hybridization techniques, they can be readily applied by one of ordinary skill in the art.

A probe and sample are combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting. As is well known in the art, if the probe molecule and nucleic acid sample hybridize by forming a strong non-covalent bond between the two molecules, it can be reasonably assumed that the probe and sample are essentially identical, or completely complementary if the annealing and washing steps are carried out under conditions of high stringency. The probe's detectable label provides a means for determining whether hybridization has occurred.

In the use of the oligonucleotides or polynucleotides as probes, the particular probe is labeled with any suitable label known to those skilled in the art, including radioactive and non-radioactive labels. Typical radioactive labels include $^{32}P$, $^{35}S$, or the like. Non-radioactive labels include, for example, ligands such as biotin or thyroxine, as well as enzymes such as hydrolases or peroxidases, or a chemiluminescer such as luciferin, or fluorescent compounds like fluorescein and its derivatives. Alternatively, the probes can be made inherently fluorescent as described in International Application No. WO 93/16094.

Various degrees of stringency of hybridization can be employed. The more stringent the conditions, the greater the complementarity that is required for duplex formation. Stringency can be controlled by temperature, probe concentration, probe length, ionic strength, time, and the like. Preferably, hybridization is conducted under moderate to high stringency conditions by techniques well know in the art, as described, for example in Keller, G. H. and M. M. Manak (1987) *DNA Probes*, Stockton Press, New York, N.Y., pp. 169-170, hereby incorporated by reference.

As used herein, moderate to high stringency conditions for hybridization are conditions which achieve the same, or about the same, degree of specificity of hybridization as the conditions employed by the current inventors. An example of high stringency conditions are hybridizing at 68° C. in 5×SSC/5× Denhardt's solution/0.1% SDS, and washing in 0.2×SSC/0.1% SDS at room temperature. An example of conditions of moderate stringency are hybridizing at 68° C. in 5×SSC/5× Denhardt's solution/0.1% SDS and washing at 42° C. in 3×SSC. The parameters of temperature and salt concentration can be varied to achieve the desired level of sequence identity between probe and target nucleic acid. See, e.g., Sambrook et al. (1989) vide infra or Ausubel et al. (1995) *Current Protocols in Molecular Biology*, John Wiley & Sons, NY, N.Y., for further guidance on hybridization conditions.

Specifically, hybridization of immobilized DNA in Southern blots with $^{32}P$-labeled gene specific probes was performed by standard methods (Maniatis et al.) In general, hybridization and subsequent washes were carried out under moderate to high stringency conditions that allowed for detection of target sequences with homology to the exemplified mega sequences. For double-stranded DNA gene probes, hybridization can be carried out overnight at 20-25° C. below the melting temperature (Tm) of the DNA hybrid in 6×SSPE 5× Denhardt's solution, 0.1% SDS, 0.1 mg/ml denatured DNA. The melting temperature is described by the following formula [Beltz, G. A. et al. (1983) *Methods of Enzymology*, R. Wu, L, Grossman and K Moldave (eds) Academic Press, New York 100:266-285].

$Tm=81.5°$ C.+16.6 Log [Na+]+0.41(+G+C)−0.61
(% formamide)−600/length of duplex in
base pairs.

Washes are typically carried out as follows: twice at room temperature for 15 minutes in 1×SSPE, 0.1% SDS (low stringency wash), and once at TM-20° C. for 15 minutes in 0.2×SSPE, 0.1% SDS (moderate stringency wash).

For oligonucleotide probes, hybridization was carried out overnight at 10-20° C. below the melting temperature (Tm) of the hybrid 6×SSPE, 5× Denhardt's solution, 0.1% SDS, 0.1 mg/ml denatured DNA. Tm for oligonucleotide probes was determined by the following formula: TM(° C.)=2 (number T/A base pairs+4(number G/C base pairs) [Suggs, S. V. et al. (1981) *ICB-UCLA Symp. Dev. Biol. Using Purified Genes*, D. D. Brown (ed.), Academic Press, New York, 23:683-693].

Washes were typically carried out as follows: twice at room temperature for 15 minutes 1×SSPE, 0.1% SDS (low stringency wash), and once at the hybridization temperature for 15 minutes in 1×SSPE, 0.1% SDS (moderate stringency wash).

In general, salt and/or temperature can be altered to change stringency. With a labeled DNA fragment >70 or so bases in length, the following conditions can be used: Low, 1 or 2×SSPE, room temperature; Low, 1 or 2×SSPE, 42° C.; Moderate, 0.2× or 1×SSPE, 65° C.; and High, 0.1×SSPE, 65° C.

Duplex formation and stability depend on substantial complementarity between the two strands of a hybrid, and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, and those methods are known to an ordinarily skilled artisan. Other methods may become known in the future.

Mutational, insertional, and deletional variants of the disclosed nucleotide sequences can be readily prepared by methods which are well known to those skilled in the art. These variants can be used in the same manner as the exemplified primer sequences so long as the variants have substantial sequence homology with the original sequence. As used herein, substantial sequence homology refers to homology which is sufficient to enable the variant polynucleotide to function in the same capacity as the polynucleotide from which the probe was derived. Preferably, this homology is greater than 80%, more preferably, this homology is greater than 85%, even more preferably this homology is greater than 90%, and most preferably, this homology is greater than 95%. The degree of homology or identity needed for the variant to function in its intended capacity depends upon the intended use of the sequence. It is well within the skill of a person trained in this art to make mutational, insertional, and deletional mutations which are equivalent in function or are designed to improve the function of the sequence or otherwise provide a methodological advantage. Methods for confirming antibiotic resistance are known in the art.

Polymerase Chain Reaction (PCR) is a repetitive, enzymatic, primed synthesis of a nucleic acid sequence. This procedure is well known and commonly used by those skilled in this art [see Mullis, U.S. Pat. Nos. 4,683,195, 4,683,202, and 4,800,159; Saiki et al. (1985) *Science* 230: 1350-1354]. PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. Since the extension product of each primer can serve as a template for the other primer, each cycle essentially doubles the amount of DNA template produced in the previous cycle. This results in the exponential accumulation of the specific target fragment, up to several million-fold in a few hours. By using a thermostable DNA polymerase such as the Taq polymerase, which is isolated from the thermophilic bacterium *Thermus aquaticus*, the amplification process can be completely automated. Other enzymes which can be used are known to those skilled in the art.

It is well known in the art that the polynucleotide sequences of the present invention can be truncated and/or mutated such that certain of the resulting fragments and/or mutants of the original full-length sequence can retain the desired characteristics of the full-length sequence. A wide variety of restriction enzymes which are suitable for generating fragments from larger nucleic acid molecules are well known. In addition, it is well known that Bal31 exonuclease can be conveniently used for time-controlled limited digestion of DNA. See, for example, Maniatis (1982) *Molecular Cloning: A Laboratory Manual*, Cold Spring Harbor Laboratory, New York, pages 135-139, incorporated herein by reference. See also Wei et al. (1983 *J. Biol. Chem.* 258: 13006-13512. By use of Bal31 exonuclease (commonly referred to as "erase-a-base" procedures), the ordinarily skilled artisan can remove nucleotides from either or both ends of the subject nucleic acids to generate a wide spectrum of fragments which are functionally equivalent to the subject nucleotide sequences. One of ordinary skill in the art can, in this manner, generate hundreds of fragments of controlled, varying lengths from locations all along the original Mega sequence. The ordinarily skilled artisan can routinely test or screen the generated fragments for their characteristics and determine the utility of the fragments as taught herein. It is also well known that the mutant sequences of the full length sequence, or fragments thereof, can be easily produced with site directed mutagenesis. See, for example, Larionov, O. A. and Nikiforov, V. G. (1982) *Genetika* 18(3):349-59; Shortle, D. et al. (1981) *Annu. Rev. Genet.* 15:265-94; both incorporated herein by reference. The skilled artisan can routinely produce deletion-, insertion-, or substitution-type mutations and identify those resulting mutants which contain the desired characteristics of the full length wild-type sequence, or fragments thereof, i.e., those which retain activity.

DNA sequences having at least 90, or at least 95% identity to the recited coding sequences of SEQ ID NO:1 are considered the most preferred equivalents to the sequences of SEQ ID NO:1. Following the teachings herein and using knowledge and techniques well known in the art, the skilled worker will be able to make a large number of operative embodiments having equivalent DNA sequences to those listed herein without the expense of undue experimentation.

As used herein percent sequence identity of two nucleic acids is determined using the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul et al. (1990) *J. Mol. Biol.* 215:402-410. BLAST nucleotide searches are performed with the NBLAST program, score=100, wordlength=12, to obtain nucleotide sequences with the desired percent sequence identity. To obtain gapped alignments for comparison purposes, Gapped BLAST is used as described in Altschul et al. (1997) *Nucl. Acids. Res.* 25:3389-3402. When utilizing BLAST and Gapped BLAST programs, the default parameters of the respective programs (NBLAST and XBLAST) are used. See the ncbi.nih.gov. site on the worldwide web.

Monoclonal or polyclonal antibodies, preferably monoclonal, specifically reacting with a protein of interest can be made by methods well known in the art. See, e.g., Harlow and Lane (1988) *Antibodies: A Laboratory Manual*, Cold Spring Harbor Laboratories; Goding (1986) *Monoclonal Antibodies: Principles and Practice,* 2d ed., Academic Press, New York; and Ausubel et al. (1993) *Current Protocols in Molecular Biology*, Wiley Interscience/Greene Publishing, New York, N.Y.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning,* Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol.* 218, Part I; Wu (ed.) (1979) *Meth. Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkley; Schleif and Wensink (1982) *Practical Methods in Molecular Biology*; Glover (ed.) (1985) *DNA Cloning* Vol. I and II, IRL Press, Oxford, UK; Hames and Higgins (eds.) (1985) *Nucleic Acid Hybridization*, IRL Press, Oxford, UK; Setlow and Hollaender (1979) *Genetic Engineering: Principles and Methods*, Vols. 1-4, Plenum Press, New York; and Ausubel et al. (1992) *Current Protocols in Molecular Biology*, Greene/Wiley, New York, N.Y. Abbreviations and nomenclature, where employed, are deemed standard in the field and commonly used in professional journals such as those cited herein.

All references cited in the present application are incorporated by reference herein to the extent that there is no inconsistency with the present disclosure.

The following examples are provided for illustrative purposes, and are not intended to limit the scope of the invention as claimed herein. Any variations in the exemplified articles which occur to the skilled artisan are intended to fall within the scope of the present invention.

EXAMPLES

Example 1

S. pneumoniae Isolates

Erythromycin-resistant isolates *S. pneumoniae* were obtained as a part of an active, population-based surveillance for invasive bacterial pathogens in metropolitan Atlanta. The specific collection methods have been previously described [20]. Briefly, all sterile-site isolates of *S. pneumoniae* (n=4148) were collected from the eight county metropolitan Atlanta area, Georgia Health District 3, (population 2.7 million: 1997 census) from 1994 to 1999. Laboratory audits were conducted to assess accuracy, and case report forms were generated on all cases. A subset of 336 erythromycin-resistant isolates (MIC=4 µg/ml), identified consecutively by the surveillance in 1994-1996 and in 1998, was studied for the presence of mefE and ermAM [13]. Eighty-nine mefE-containing isolates (MIC≧4 µg/ml) recovered from patients with invasive pneumococcal disease from January 1994 to February 1996 and the 129 mefE-containing isolates recovered in 1998 formed the collection of isolates used in of this study. These isolates included GA3488 (serotype 6A), GA2551 (serotype 14), GA2254 (serotype 14), GA4375 (serotype 19F) and GA4175 (serotype 19A). The erythromycin sensitive (mefE-, ermAM-) pneumococcal laboratory strain R6 was also used. Isolates were grown in Todd-Hewitt broth with 0.5% yeast extract. Antimicrobial susceptibility of isolates collected from this surveillance was determined by guidelines established by the National Committee for Clinical Laboratory Standards (NCCLS) [21]. Serotyping was performed as previously described [20].

Example 2

DNA Isolation

Genomic DNA was isolated from *S. pneumoniae* by one of two methods. Crude preparations of DNA were obtained by boiling bacterial pellets for ten minutes in 100 mM NaCl, 10 mM Tris-HCl (pH 8.3), 1 mM EDTA, and 1% Triton X-100. Higher purity DNA was prepared by sequential incubations of cell suspensions in lysozyme and RNase (Sigma, St. Louis, Mo.), phenol/chloroform purification and ethanol precipitation as described by Nath [22].

Example 3

PCR-Based Detection of mefE

Nucleotide primers used in PCR and DNA sequencing are shown in Table 1. Primer set KG5F and KG5R2 was used to define 345 bp of mefE [12]. KG17R was also paired with KG5F to amplify mefE, resulting in a 1355 bp product. PCR amplification consisted of 35 cycles with a 30 second denaturation at 95° C., a 30 second anneal at 60° C., and extension for 1 minute at 72° C. in a GeneAmp PCR System 9600 thermal cycler (Perlin-Elmer Applied Biosystems, Foster City, Calif.). Each reaction contained 500 ng of template DNA, 50 mM KCl, 10 mM Tris-HCl (pH 8.3), 200 µM each of deoxyribonucleoside triphosphate, 2.5 U Taq DNA polymerase (Perkin-Elmer Applied Biosystems, Foster City, Calif.), 1.5 mM $MgCl_2$ and 1.5 µM of each primer. PCR products were visualized by 1.2% agarose gel electrophoresis and ethidium bromide staining.

Example 4

Single Specific Primer Polymerase-Chain Reaction (SSP-PCR)

Restriction digests of chromosomal DNA from GA3488 were ligated with SmaI restricted pUC18. Twenty units of HaeIII (New England Biolabs, Beverly, Mass.) were used to digest 100 µg of chromosomal DNA at 37° C. for 2 hours.

The vector was prepared by digesting 2 µg of pUC18 with 10 U of SmaI (New England Biolabs, Beverly, Mass.) at room temperature for 1 hour. One unit of shrimp alkaline phosphatase (USB, Cleveland, Ohio) was then added, and the vector was incubated for an additional hour at 37° C. Both the vector and chromosomal insert were heat inactivated at 70° C. for twenty minutes. The ligation reaction consisted of the pUC18 vector and chromosomal insert in a 1:4 ratio incubated at 4° C. with 400 U T4 ligase (New England Biolabs, Beverly, Mass.). Unsequenced regions of DNA flanking mefE were amplified using a single insert-specific primer paired with a primer specific to the cloning site of pUC18, CM7 as described above. Initially, KG7 and KG8 were used as the mefE-specific primers based on GenBank accession no. SPU83667. Further characterization of the region upstream from mefE was accomplished with primers KG9 and KG12. Additional SSP-PCR of the downstream sequence used primers KG16, KG18, KG20F, KG24 and KG26F.

Example 5

DNA Sequence Analysis

PCR products were purified using QiaQuick columns according to the manufacturer's instructions (Qiagen, Santa Clara, Calif.). Automated sequencing was performed with Applied Biosystems PRISM 377 equipment using the same primers as those for PCR. Sequence analysis was conducted with GeneJockey II (BioSoft, Cambridge, UK) and BLAST version 2.0. Preliminary pneumococcal sequence data was obtained from The Institute for Genomic Research (TIGR) website.

Example 6

RNA Isolation and RT-PCR

Total RNA was obtained from strains GA3488 and GA2551 using the RNeasy Mini Kit following the manufacturer's instructions (Qiagen, Santa Clara, Calif.). Reverse transcription was performed with Gene Amp according to Perkin-Elmer's protocol with primer KG5F (Perkin-Elmer Applied Biosystems, Foster City, Calif.). PCR was performed as described above using KG5F as the forward primer and KG5R2 or KG18R as the reverse primer.

Example 7

Pulsed Field Gel Electrophoresis (PFGE)/Southern Hybridizations

Pneumococci from overnight cultures were suspended in low melting agarose at a concentration of ~0.5 McFarland units to form plugs, incubated in 500 mM EDTA/1% N-lauroyl sarcosine overnight at 55° C. and digested with SmaI (New England Biolabs, Beverly, Mass.) at room temperature for 2 hours following the protocol described by McEllistrem et al. [23]. PFGE was then performed in a 1% agarose (SeaKem GTG agarose; FMC Bioproducts, Rockland, Me.) 0.5× Tris-borate-EDTA buffer using the CHEF-DR II electrophoresis system (Bio-Rad Laboratories, Hercules, Calif.) at 6 V/cm, 1-20 second switch time, for 22 hours. The gel was then stained with ethidium bromide and photographed with ultraviolet illumination. Dendograms were constructed with the BioImage electrophoresis analysis system and software package [24].

Gels which were used for Southern transfer were subjected a 30 minute acid depurination (0.25 M HCl), followed by a 30 minute base treatment (1.5 M NaCl, 0.5 M NaOH) and neutralization (1.5 M NaCl, 0.5 M Tris-HCl). Gels were equilibrated in transfer buffer (2×SSC) prior to overnight capillary blotting [25]. DNA was fixed to the membrane by UV crosslinking and prehybridized for at least two hours at 65° C. Membranes were hybridized with a mef probe in 5×SSC, 1% blocking reagent, 0.1% N-laurosarcosine and 0.02% SDS at 65° C. overnight. Chemiluminescent detection was performed with Genius 3 system according to the manufacturer's instructions (Boehringer Mannheim, Indianapolis, Ind.).

Random prime labeling with digoxigenin was performed with Genius 2 according to the manufacturer's instructions (Boehringer Mannheim Corp., Indianapolis, Ind.). A 1680 bp template spanning most of mefE and mel was generated by PCR using primers KG17R and KG5F. PCR amplification was performed as described above.

Example 8

Transformation

A 6278 bp PCR product containing mega and flanking chromosomal sequence was generated with primers KG25F and KG33R. The unencapsulated laboratory strain, R6, grown to an optical density of 1.8 at 650 nm in C+Y media, was transformed with 10 µg/ml of the PCR product in the presence of 50 ng/ml competence stimulating peptide at 30° C. for 45 minutes [26,27]. Transformants were selected on TSA+5% sheep blood agar plates with 1 µg/ml erythromycin.

Resistance to macrolide and/or streptogramin B antibiotics due to a mega-related element (one having at least 70% nucleotide sequence identity with SEQ ID NO:1) can be predicted in a clinical isolate or in a patient suffering from an infection with a gram positive bacterium when sequences in a clinical isolate, a patient specimen comprising the infecting bacterium or bacteria grown from a patient specimen are observed which hybridize specifically to nucleic acid molecule(s) of sequence(s) of at least 20 nucleotides from SEQ ID NO:1, where the at least 20 nucleotides are unique to mega. One of skill in the art knows to avoid sequences which are shared among other macrolide or streptogramin B efflux sequences other than those of mega or other proteins with significant sequence homology to sequences from sources other than mega Preferably, the sequences of the nucleic acid molecule(s) to detect mega related antibiotic resistance sequences are unique to the mega genetic element. Specific hybridization to one or more mega derived sequences can be observed by signals obtained for DNA:DNA or RNA:DNA hybridization in a conventional hybridization assay (blot or liquid) or hybridization can be detected using sensor or micrarray/microchip technology. Additionally, amplification products can be prepared in polymerase chain reaction assays.

TABLE 1

Oligonucleotide primers used in polymerase chain reaction and sequencing

| Primer | Sequence (5'→3') | Sequence used for primer design | Position mega | Primer paired with | SEQ ID NO: |
|---|---|---|---|---|---|
| KG5F | AGTATCATTAATCACTAGTGC | ORF 1 (mef) | 1181-1201 | KG5R2; KG17R | 17 |
| KG5R2 | TTCTTCTGGTACTAAAAGTGG | ORF 1 (mef) | 1506-1525 | KG5F | 18 |
| KG17R | CTTCACGGTCTAAATGGCTCG | ORF 2 (mel) | 2841-2861 | KG5F | 19 |
| CM7 | CCAGTCACGACGTTGTAAAACG | pUC19 | — | KG7-26F | 20 |
| KG7 | TAGACAAGACCATCGCAGATCCT | ORF 1 (mef) | 1244-1266 | CM7 | 21 |
| KG8 | GTATCATGTCACTTGCTATGCC | ORF 1 mef) | 2182-2203 | CM7 | 22 |
| KG9 | CCTCACCGTAACTAATGAATGCTC | Upstream from mef | 911-934 | CM7 | 23 |
| KG12 | CATAGACTGTAACGCTCTGG | Upstream from mef | 653-672 | CM7 | 24 |
| KG16 | CACTTGTAGGCAAGCTAGGTGT | ORF 2 (mel) | 2715-2736 | CM7 | 25 |
| KG18 | CATACCCTATAGTCGGTGCAG | ORF 2 (mel) | 3342-3361 | CM7 | 26 |
| KG20 | CTGGTTCTGGTTGGCGACTC | Downstream from mel | 3955-3972 | CM7 | 27 |
| KG24 | GTATCCTGGTACTCTCTTGCTG | ORF 4 | 4646-4667 | CM7 | 28 |
| KG26F | TCTCACTGCACCAGAGGTG | ORF 5 | 5284-5301 | CM7 | 29 |
| KG25F | GGATACCCAGTCTCCTGAAG | TIGR SP-66 | — | KG33R | 30 |
| KG33R | GACTGGCAATGCTAGCGGC | TIGR SP-66 | — | KG25F | 31 |

NOTE.
mega, Macrolide efflux genetic assembly (a chromosomal insertion element)
TIGR, The Institute for Genomic Research.

TABLE 2

Macrolide efflux genetic assembly (mega; a chromosomal insertion element) insertions in clinical isolates of macrolide-resistant Streptococcus pneumoniae containing mefE (n – 89).

| Serotype | Class I (n = 14) | Class II (n~55) | Class III (n = 3) | Class IV (n = 1) |
|---|---|---|---|---|
| 6A | 11 | 6 | 0 | 0 |
| 6B | 0 | 12 | 0 | 0 |
| 14 | 1 | 27 | 1 | 1 |
| 19A | 1 | 2 | 2 | 0 |
| 19F | 0 | 1 | 0 | 0 |
| 23F | 0 | 1 | 0 | 0 |
| NT | 1 | 6 | 0 | 0 |

NOTE:
mefE-Containing invasive pneumococcal strains were isolated in Atlanta, 1994-1996. Class I-IV are genomic locations of mega pneumococcal chromosome (FIG. 5). Sixteen of 89 isolates were undefined insert type by polymerase chain reaction.
NT, nontypeable.

REFERENCES

1. Schito, G. C. et al. J. Chemother. 1997; 9:18-28.
2. Carbon, C. and Poole, M. D. J. Chemother. 1999; 11:107-18.
3. Doern, G. V. et al. Clin. Infect. Dis. 1998; 27:764-70.
4. Klugman, K. P. et al. J. Antimicrob. Chemother. 1998; 42:729-34.
5. Hickey, M. L. et al. In: 38th Interscience conference on Antimicrobial Agents and Chemotherapy (San Diego). Washington, D.C.: American Society for Microbiology, 1998:172-3.
6. Weisblum, B. Antimicrob. Agents Chemother. 1995; 39:577-85.
7. Arthur, M. et al. Antimicrob. Agents Chemother. 1987; 31:404-9.
8. Trieu-Cuot, P. et al. Nucleic Acids Res 1990; 18:3660.
9. Sutcliffe, J. et al. Antimicrob. Agents Chemother. 1996; 40:1817-24.
10. Clancy, J. et al. Mol. Microbiol. 1996; 22:867-79.
11. Roberts, M. C. et al. Antimicrob. Agents Chemother. 1999; 43:2823-30.
12. Sutcliffe, J. et al. Antimicrob. Agents Chemother. 1996; 40:2562-6.
13. Gay, K. et al. J. Infect. Dis. 2000; 182:1417-24.
14. Santagati, M. et al. Antimicrob. Agents Chemother. 2000; 44:2585-7.
15. Luna, V. A. et al. Antimicrob. Agents Chemother. 2000; 44:2503-6.
16. Oster, P. et al. Antimicrob. Agents Chemother. 1999; 43:2510-2.
17. Johnston, N. J. et al. Antimicrob. Agents Chemother. 1998; 42:2425-6.
18. Shortridge, V. D. et al. Diagn. Microbiol. Infect. Dis. 1996; 26:73-8.
19. Waites, K. et al. J. Clin. Microbiol. 2000; 38:1731-4.
20. Hofmann, J. et al. N. Engl. J. Med. 1995; 333:481-6.
21. National Committee for Laboratory Standards. Performance standards for antimicrobial susceptibility testing: eighth informational supplement NCCLS document M100-SB, Wayne, Pa.: 1998.
22. Nath K. Nucleic Acids Res 1990; 18:6462.
23. McEllistrem, M. C. et al. J. Clin. Microbiol. 2000; 38:351-3.
24. Swaminathan, B. J. Clin. Microbiol. 1996; 34:1468-73.
25. Sambrook, J. et al. Molecular cloning: A laboratory manual. Cold Spring Harbor, N.Y.: Cold Spring Harbor Laboratory Press, 1989.
26. Gurney, T. J. and Fox, M. S. J. Mol. Biol. 1968; 32:83-100.

27. Havarstein, L. S. et al. Proc. Natl. Acad. Sci. USA 1995; 92:11140-4.
28. Garvey, P. et al. Appl. Environ. Microbiol. 1997; 63:1244-51.
29. Munoz-Najar, U. J. Bacteriol. 1999; 181:2782-8.
30. Walker G. C. The SOS Response of *Escherichia coli*. In: F. C. Neidhardt and R. Curtiss, eds. *Escherichia Coli and Salmonella*: Cellular and Molecular Biology. Washington D.C.: American Society for Microbiology, 1996; pgs. 1400-16.
31. Tenover, F. C. et al. J. Clin. Microbiol. 1995; 33:2233-9.
32. Campbell, E. A. et al. Mol. Microbiol. 1998; 27:929-39.
33. Claverys, J. P. et al. Gene 1995; 164:123-8.
34. Tait-Kamradt, A. et al. Antimicrob. Agents Chemother. 1997; 41:2251-5.
35. Ross, J. I. et al. Mol. Microbiol. 1990; 4:1207-14.
36. Ross, J. I. et al. Gene 1996; 183:143-8.
37. Linton, K. J. et al. Mol. Microbiol. 1998; 28:5-13.
38. Walker, J. E. et al. EMBO J. 1982; 1:945-51.
39. Hyde, S. C. et al. Nature 1990; 346:362-5.
40. Wootton, J. C. et al. Protein Eng. 1989; 2:535-43.
41. Claverys, J. P. and Martin, B. Mol. Microbiol. 1998; 29:1126-7.
42. Corso, A. et al. Microb. Drug Resist. 1998; 4:325-37.
43. McDougal, L. K. et al. Antimicrob. Agents Chemother. 1992; 36:2176-84.

What is claimed is:

1. An isolated nucleic acid molecule consisting of a nucleotide sequence of a macrolide efflux genetic assembly, wherein the nucleotide sequence has at least about 95% nucleotide sequence identity with SEQ ID NO:1, and wherein the macrolide efflux genetic assembly determines resistance to macrolide and streptogramin B antibiotics.

2. The isolated nucleic acid molecule of claim 1 wherein the macrolide to which resistance is determined is at least one of erythromycin, clarithromycin and azithromycin.

3. The isolated nucleic acid molecule of claim 1 wherein the streptogramin B to which resistance is determined is at least one of dalfopristin and quinupristin.

4. The isolated nucleic acid molecule of claim 3 wherein the streptogramin B resistance is determined by a nucleotide sequence encoding the protein set forth by in SEQ ID NO:3.

5. The isolated nucleic acid molecule of claim 1 wherein said nucleotide sequence is SEQ ID NO:1.

6. A method of identifying a composition which inhibits efflux of a macrolide and/or a streptogramin B antibiotic by a bacterium, wherein the bacterium comprises the isolated nucleic acid molecule of claim 1;

said method comprising the steps of:
(a) contacting the bacterium with a composition comprising a test compound and a macrolide or streptogramin B antibiotic,
wherein the test compound is at a subinhibitory concentration such that, in the absence of the macrolide or streptogramin B antibiotic, the growth of the bacterium is not inhibited, and
wherein the macrolide or streptogramin B antibiotic is at a subinhibitory concentration such that, in the absence of the test compound, the growth of the bacterium is not inhibited; and
(b) determining the effect of the composition on cell growth, whereby the composition is identified as an inhibitor of efflux of a macrolide or a streptogramin B antibiotic when the composition inhibits growth of the bacterium.

7. The method of claim 6 wherein the macrolide to which resistance is determined is at least one of erythromycin, clarithromycin and azithromycin.

8. The method of claim 6 wherein the streptogramin B to which resistance is determined is at least one of dalfopristin and quinupristin.

9. The method of claim 6 wherein said isolated nucleotide sequence is SEQ ID NO:1.

10. The method of claim 6 wherein the bacterium is a gram positive bacterium.

11. The method of claim 10 wherein the bacterium is a species of *Streptococcus*, *Staphylococcus* or *Enterococcus*.

* * * * *

SEQUENCE LISTING

<160> NUMBER OF SEQ ID NOS: 34

<210> SEQ ID NO 1
<211> LENGTH: 5532
<212> TYPE: DNA
<213> ORGANISM: Streptococcus pneumoniae

<400> SEQUENCE: 1

```
catgttgagg cggtaagttt gctagtcaag gagtaaaacg acgaagatta gcatttactt      60
ccgcccatgc gatagctgtc cgtgattgac aagtgctagc acgcagacag aacggagata     120
gcgaaccgct gagtgtgtcg ctctgctcgt aaaagcttag aaacctttga acgaaaggga     180
taatgaaagc cttgattgca aggcttttg ctttatggtg ggtaagtatc agagtgagaa      240
aattttggga atgagtagaa gtgatagcta gaaattatca gtttctattt ccatttaccc     300
tgtgggtacg tgtttgtttc cattgacaag gagtttgtgg aatagaaat gtacccacct      360
tgtttgaatc aagtgaagtg tagttgaagg aaatctgttg aaagcaatac ttcattttac     420
cgaataagta ataatttagg caacttcaaa tcgattaaaa aaaactattt taaaggttaa     480
gagtagacaa aaattgtcca ctctttttg caaactcaat ttatcaataa atgaaatgag      540
ggaatgtaaa atgaaatatt ttgaggttga gttagaaaat cctgatgaat ttttaaaact     600
acaaacagaa gattttgtga aaagctaatc gcttgctact aaggaaaata atccagagcg     660
ttacagtcta tgaagaaaac ttcgtcatat cctttaaatc tggcatcgaa ttggaagtat     720
gagtctcatt ccataacttt tatattgaac atatcatctt gttgtgttat actataaatt     780
gatataaaca aagatgtagg aggaaccgaa actatgacga cctcaatgcg tttaagataa     840
gctggcaata aaaaagcag aatctatacc cgatgatagg cttttttgtt gtgcttattt      900
atacgatatt gagcattcat tagttacggt gaggatattg gttatttaac tataccttta     960
tttaactata cctttattta actatgtctt taatatgaat gtttccaaat tgtatgtatg    1020
cagaccaaaa gccacattgt ggatttaggc ctgcatttt ttattgccta taatgctatt     1080
caaaatagaa atttaagcaa aataatatgc aggagataat ataaatggaa aaatacaaca    1140
attgaaacg aaaattttat gcaatatggg cagggcaagc agtatcatta atcactagtg     1200
ccatcctgca aatggcgatt atttttacc ttacagaaaa aacaggatct gcgatggtct    1260
tgtctatggc ttcattagta ggttttttac cctatgcgat tttgggacct gccattggtg    1320
tgctagtgga tcgtcatgat aggaagaaga taatgattgg tgccgattta attatcgcag    1380
cagctggtgc agtgcttgct attgttgcat tctgtatgga gctacctgtc tggatgatta    1440
tgatagtatt gtttatccgt agcattggaa cagctttttca taccccagca ctcaatgcgg    1500
```

```
ttacaccact tttagtacca gaagaacagc taacgaaatg cgcaggctat agtcagtctt   1560
tgcagtctat aagctatatt gttagtccgg cagttgcagc actcttatac tccgtttggg   1620
atttaaatgc tattattgcc atcgacgtat tgggtgctgt gattgcatct attacggtag   1680
caattgtacg tatacctaag ctgggtaatc aagtgcaaag tttagaacca aatttcataa   1740
gggagatgaa agaaggagtt gtggttctga gacaaaacaa aggattgttt gccttattac   1800
tcttaggaac actatatact tttgtttata tgccaatcaa tgcactattt cctttaataa   1860
gcatggaaca ctttaatgga acgcctgtgc atatttctat tacggaaatt tcctttgcat   1920
ttgggatgct agcaggaggc ttattattag gaagattagg gggcttcgaa aagcatgtat   1980
tactaataac aagttcattt tttataatgg ggaccagttt agccgtttcg ggaatacttc   2040
ctccaaatgg atttgtaata ttcgtagttt gctgtgcaat aatggggctt tcggtgccat   2100
tttatagcgg tgtgcaaaca gctctttttc aggagaaaat taagcctgaa tatttaggac   2160
gtgtattttc tttgatcgga agtatcatgt cacttgctat gccaattggg ttaattcttt   2220
ctggattctt tgctgataaa atcggtgtaa atcattggtt tttactatca ggtattttaa   2280
ttattggcat tgctatagtt tgccaaatga taactgaggt tagaaaatta gatttaaaat   2340
aaacaatatt ggaggaatat ttatgtatct tattttcatg taactcttcc tgctaaaatc   2400
gcagggtttt ccctgcatac aagcaaatga aagcatgcga ttatagacag gaggaaatgt   2460
tatggaatta atattaaaag caaaagacat tcgtgtggaa ttcaaaggac gcgatgtttt   2520
agatataaat gaattagaag tatatgatta tgaccgtatt ggtttagtag gagcaaatgg   2580
tgctggaaaa agcactttac tcagggtact tttaggagaa ttaactcccc aggatgtaa    2640 aatgaatcgt ctgggtgaac ttgcctatat tccccagttg gacgaagtaa ctctgcagga   2700
ggaaaaagat tttgcacttg taggcaagct aggtgttgag caattaaata tacagactat   2760
gagcggtggt gaagaaacaa ggcttaaaat agcacaggcc ttatcggcac aggttcatgg   2820
tattttagcg gatgaaccta cgagccattt agaccgtgaa ggaattgatt ttctaatagg   2880
acagctaaaa tatttacag gtgcactgtt agttattagc catgaccgct attttcttga    2940
tgaaatagta gataaaatat gggaactgaa agatggcaaa atcactgagt attggggaaa   3000
ctattctgat tatcttcgtc agaaagagga agaacgtaag agccaagctg cagaatacga   3060
acaatttatt gcggaacgtg cccgattgga aagggctgcg gaggaaaagc gaaaacaggc   3120
tcgtaaaata gaacagaagg caaaaggttc ttcaaagaaa aaaagtactg aagacggagg   3180
gcgtttagct catcaaaaat caataggaag taaggaaaaa aagatgtata atgctgctaa   3240
aaccctagag cacaggattg cggccttagg aaaagtagaa gctccggaag gcattcgcag   3300
aattcgtttc aggcaaagta aagcattgga gctccataat ccatacccta tagtcggtgc   3360
agaaattaat aaagtatttg gggataaggc tctgtttgaa aatgcatctt ttcaaattcc   3420
gttaggagca aaagtggcgt taactggtgg taatggaatc ggaaaaacaa ctttaatcca   3480
aatgatctta aaccatgaag aaggaatttc tatttcgcct aaggcaaaaa taggttactt   3540
tgcacagaat ggttacaagt acaacagtaa tcagaatgtt atggagttta tgcagaagga   3600
ttgtgactac aatatatcag aaattcgttc agtgctagca tctatggggt tcaaacagaa   3660
cgatattgga aaaagtttat ctgttttaag cggtggagaa attataaaat tgttgcttgc   3720
taaaatgctc atgggtagat ataacatcct aataatggat gaacccagta acttccttga   3780
cataccaagt ttagaggctt tggaaatact aatgaaggag tacaccggaa ctatcgtgtt   3840
tatcacccac gataaacgat tactcgaaaa tgtagcagat gtagtttatg aaattagaga   3900
```

-continued

```
taagaaaata aatctgaaac attaaattta aggtagtcgc tggtcagtaa tagtctgttc    3960
tggttggcga ctccattgtt aaagagtata aagactttag attttatgaa tattaaaaat    4020
aggaacagtc aattgaactg ctcctatttt tctgctaaat atattgtagt tttcttatat    4080
gtataatgat agattagcgg attctcatct acggtactta cttcaaatat gaagaagtga    4140
tcgcggttat ctctggactt ttccttattg aggacaaagt aattcttacg tgaagtcgcc    4200
attgttttta ggatatcatc agttaggaag gtcaatggaa tattcatgtt agagtagcgg    4260
tagaagtcac gttcaaaatc ttggtagctc tcgctataat agtccatttg taggtgatta    4320
cgctgaaact caagctgatt catagagcac ctcctcgaca agttcaatac taataatgtc    4380
ttttaatttc aaattgatgt gacctgttgt agttttatc aaaatgaaat ctttggtcag    4440
acttggtatt gttccagtgt aggaaacacg cttgtttttt tcaatcactt gaatgcgtgt    4500
gcgtagctgc ccggcgtata cttgactgag gagtaataat ttcttctcta gtgataagtc    4560
agacatgtac gttactttgt tgtatcatc agagagtgct gatgcatgtt cagataggaa    4620
aaagcccatc cattttttgca tctttgtatc ctggtactct cttgctgatt gaatggtaa    4680 aattggaacg gtcaatcata tcaaatcctt tctatgcaga ggcaagggta ttttatcaa    4740 attgaatcgt aaaaccttga attccccac ctgtgtaaca ttctttaaag cgattgatta    4800
cctcagtata gattatcaca gatgagcttg ttggcttaat gctaaatgta aattccaatg    4860
gtaatcggtt ttcagattta gcatgtacta gtcgtatcga tatttcagtt gttttgagtt    4920
ttctctgacg aagttttgaa gttgctgttt caacgattcc atgtaaaaat ctttcaagca    4980
tttcaatatc attacatcct ttgctacgga tttctgaaaa ttgtactgta ttttttttctt    5040 gtttcatttt aatccctcca atccacccgc ggaatgacca ccgataagtt tactgcgttc    5100
aatatttctg gaaccttcag ttaggacggt tccttttgt atggctaaaa aaccaaactg    5160
ttctctgaca acatcaatag ctgtctgaag tctattatct ttttcaattt gttctacatc    5220
atcaaagagt gatagtagag tatagctttc atctacgaag ccactataag atacaccaat    5280
ttgtctcact gcaccagagg tgtatttttt cggaataata caagtacatg actcacccat    5340
tgttttgggg agatttgcgg gttcaatttt attctgagca tttatagatt ttttcatctc    5400
agtcctagaa tagccaatat gaatagaaac gacagtagtc aatactaggg ctactgttcc    5460
gttccacagt atcatttaaa aatcattttc acacccttc gtctattagt atagaagaaa    5520
gctctcagca ca                                                        5532
```

<210> SEQ ID NO 2
<211> LENGTH: 405
<212> TYPE: PRT
<213> ORGANISM: Streptococcus pneumoniae

<400> SEQUENCE: 2

```
Met Glu Lys Tyr Asn Asn Trp Lys Arg Lys Phe Tyr Ala Ile Trp Ala
  1               5                  10                  15

Gly Gln Ala Val Ser Leu Ile Thr Ser Ala Ile Leu Gln Met Ala Ile
             20                  25                  30

Ile Phe Tyr Leu Thr Glu Lys Thr Gly Ser Ala Met Val Leu Ser Met
         35                  40                  45

Ala Ser Leu Val Gly Phe Leu Pro Tyr Ala Ile Leu Gly Pro Ala Ile
     50                  55                  60

Gly Val Leu Val Asp Arg His Asp Arg Lys Lys Ile Met Ile Gly Ala
 65                  70                  75                  80
```

```
Asp Leu Ile Ile Ala Ala Gly Ala Val Leu Ala Ile Val Ala Phe
                85                  90                  95

Cys Met Glu Leu Pro Val Trp Met Ile Met Ile Val Leu Phe Ile Arg
            100                 105                 110

Ser Ile Gly Thr Ala Phe His Thr Pro Ala Leu Asn Ala Val Thr Pro
        115                 120                 125

Leu Leu Val Pro Glu Glu Gln Leu Thr Lys Cys Ala Gly Tyr Ser Gln
    130                 135                 140

Ser Leu Gln Ser Ile Ser Tyr Ile Val Ser Pro Ala Val Ala Ala Leu
145                 150                 155                 160

Leu Tyr Ser Val Trp Asp Leu Asn Ala Ile Ala Ile Asp Val Leu
                165                 170                 175

Gly Ala Val Ile Ala Ser Ile Thr Val Ala Ile Val Arg Ile Pro Lys
                180                 185                 190

Leu Gly Asn Gln Val Gln Ser Leu Glu Pro Asn Phe Ile Arg Glu Met
            195                 200                 205

Lys Glu Gly Val Val Val Leu Arg Gln Asn Lys Gly Leu Phe Ala Leu
        210                 215                 220

Leu Leu Leu Gly Thr Leu Tyr Thr Phe Val Tyr Met Pro Ile Asn Ala
225                 230                 235                 240

Leu Phe Pro Leu Ile Ser Met Glu His Phe Asn Gly Thr Pro Val His
                245                 250                 255

Ile Ser Ile Thr Glu Ile Ser Phe Ala Phe Gly Met Leu Ala Gly Gly
                260                 265                 270

Leu Leu Leu Gly Arg Leu Gly Gly Phe Glu Lys His Val Leu Leu Ile
            275                 280                 285

Thr Ser Ser Phe Phe Ile Met Gly Thr Ser Leu Ala Val Ser Gly Ile
    290                 295                 300

Leu Pro Pro Asn Gly Phe Val Ile Phe Val Val Cys Cys Ala Ile Met
305                 310                 315                 320

Gly Leu Ser Val Pro Phe Tyr Ser Gly Val Gln Thr Ala Leu Phe Gln
                325                 330                 335

Glu Lys Ile Lys Pro Glu Tyr Leu Gly Arg Val Phe Ser Leu Ile Gly
            340                 345                 350

Ser Ile Met Ser Leu Ala Met Pro Ile Gly Leu Ile Leu Ser Gly Phe
        355                 360                 365

Phe Ala Asp Lys Ile Gly Val Asn His Trp Phe Leu Leu Ser Gly Ile
    370                 375                 380

Leu Ile Ile Gly Ile Ala Ile Val Cys Gln Met Ile Thr Glu Val Arg
385                 390                 395                 400

Lys Leu Asp Leu Lys
                405

<210> SEQ ID NO 3
<211> LENGTH: 487
<212> TYPE: PRT
<213> ORGANISM: Streptococcus pneumoniae

<400> SEQUENCE: 3

Met Glu Leu Ile Leu Lys Ala Lys Asp Ile Arg Val Glu Phe Lys Gly
1               5                   10                  15

Arg Asp Val Leu Asp Ile Asn Glu Leu Glu Val Tyr Asp Tyr Asp Arg
                20                  25                  30

Ile Gly Leu Val Gly Ala Asn Gly Ala Gly Lys Ser Thr Leu Leu Arg
```

-continued

```
                 35                  40                  45
Val Leu Leu Gly Glu Leu Thr Pro Pro Gly Cys Lys Met Asn Arg Leu
 50                  55                  60

Gly Glu Leu Ala Tyr Ile Pro Gln Leu Asp Glu Val Thr Leu Gln Glu
 65                  70                  75                  80

Glu Lys Asp Phe Ala Leu Val Gly Lys Leu Gly Val Glu Gln Leu Asn
                 85                  90                  95

Ile Gln Thr Met Ser Gly Glu Glu Thr Arg Leu Lys Ile Ala Gln
                100                 105                 110

Ala Leu Ser Ala Gln Val His Gly Ile Leu Ala Asp Glu Pro Thr Ser
                115                 120                 125

His Leu Asp Arg Glu Gly Ile Asp Phe Leu Ile Gly Gln Leu Lys Tyr
                130                 135                 140

Phe Thr Gly Ala Leu Leu Val Ile Ser His Asp Arg Tyr Phe Leu Asp
145                 150                 155                 160

Glu Ile Val Asp Lys Ile Trp Glu Leu Lys Asp Gly Lys Ile Thr Glu
                165                 170                 175

Tyr Trp Gly Asn Tyr Ser Asp Tyr Leu Arg Gln Lys Glu Glu Arg
                180                 185                 190

Lys Ser Gln Ala Ala Glu Tyr Glu Gln Phe Ile Ala Glu Arg Ala Arg
                195                 200                 205

Leu Glu Arg Ala Ala Glu Glu Lys Arg Lys Gln Ala Arg Lys Ile Glu
                210                 215                 220

Gln Lys Ala Lys Gly Ser Ser Lys Lys Ser Thr Glu Asp Gly Gly
225                 230                 235                 240

Arg Leu Ala His Gln Lys Ser Ile Gly Ser Lys Glu Lys Lys Met Tyr
                245                 250                 255

Asn Ala Ala Lys Thr Leu Glu His Arg Ile Ala Ala Leu Gly Lys Val
                260                 265                 270

Glu Ala Pro Glu Gly Ile Arg Arg Ile Arg Phe Arg Gln Ser Lys Ala
                275                 280                 285

Leu Glu Leu His Asn Pro Tyr Pro Ile Val Gly Ala Glu Ile Asn Lys
                290                 295                 300

Val Phe Gly Asp Lys Ala Leu Phe Glu Asn Ala Ser Phe Gln Ile Pro
305                 310                 315                 320

Leu Gly Ala Lys Val Ala Leu Thr Gly Gly Asn Gly Ile Gly Lys Thr
                325                 330                 335

Thr Leu Ile Gln Met Ile Leu Asn His Glu Glu Gly Ile Ser Ile Ser
                340                 345                 350

Pro Lys Ala Lys Ile Gly Tyr Phe Ala Gln Asn Gly Tyr Lys Tyr Asn
                355                 360                 365

Ser Asn Gln Asn Val Met Glu Phe Met Gln Lys Asp Cys Asp Tyr Asn
370                 375                 380

Ile Ser Glu Ile Arg Ser Val Leu Ala Ser Met Gly Phe Lys Gln Asn
385                 390                 395                 400

Asp Ile Gly Lys Ser Leu Ser Val Leu Ser Gly Gly Glu Ile Ile Lys
                405                 410                 415

Leu Leu Leu Ala Lys Met Leu Met Gly Arg Tyr Asn Ile Leu Ile Met
                420                 425                 430

Asp Glu Pro Ser Asn Phe Leu Asp Ile Pro Ser Leu Glu Ala Leu Glu
                435                 440                 445

Ile Leu Met Lys Glu Tyr Thr Gly Thr Ile Val Phe Ile Thr His Asp
                450                 455                 460
```

```
Lys Arg Leu Leu Glu Asn Val Ala Asp Val Val Tyr Glu Ile Arg Asp
465                 470                 475                 480

Lys Lys Ile Asn Leu Lys His
            485
```

<210> SEQ ID NO 4
<211> LENGTH: 99
<212> TYPE: PRT
<213> ORGANISM: Streptococcus pneumoniae

<400> SEQUENCE: 4

```
Met Asn Gln Leu Glu Phe Gln Arg Asn His Leu Gln Met Asp Tyr Tyr
1               5                   10                  15

Ser Glu Ser Tyr Gln Asp Phe Glu Arg Asp Phe Tyr Arg Tyr Ser Asn
                20                  25                  30

Met Asn Ile Pro Leu Thr Phe Leu Thr Asp Asp Ile Leu Lys Thr Met
            35                  40                  45

Ala Thr Ser Arg Lys Asn Tyr Phe Val Leu Asn Lys Glu Lys Ser Arg
        50                  55                  60

Asp Asn Arg Asp His Phe Phe Ile Phe Glu Val Ser Thr Val Asp Glu
65                  70                  75                  80

Asn Pro Leu Ile Tyr His Tyr Thr Tyr Lys Lys Thr Thr Ile Tyr Leu
                85                  90                  95

Ala Glu Lys
```

<210> SEQ ID NO 5
<211> LENGTH: 102
<212> TYPE: PRT
<213> ORGANISM: Streptococcus pneumoniae

<400> SEQUENCE: 5

```
Met Gln Lys Trp Met Gly Phe Phe Leu Ser Glu His Ala Ser Ala Leu
1               5                   10                  15

Ser Asp Asp Thr Asn Lys Val Thr Tyr Met Ser Asp Leu Ser Leu Glu
                20                  25                  30

Lys Lys Leu Leu Leu Leu Ser Gln Val Tyr Ala Gly Gln Leu Arg Thr
            35                  40                  45

Arg Ile Gln Val Ile Glu Lys Asn Lys Arg Val Ser Tyr Thr Gly Thr
        50                  55                  60

Ile Pro Ser Leu Thr Lys Asp Phe Ile Leu Lys Thr Thr Thr Gly
65                  70                  75                  80

His Ile Asn Leu Lys Leu Lys Asp Ile Ile Ser Ile Glu Leu Val Glu
                85                  90                  95

Glu Val Leu Tyr Glu Ser
            100
```

<210> SEQ ID NO 6
<211> LENGTH: 143
<212> TYPE: PRT
<213> ORGANISM: Streptococcus pneumoniae

<400> SEQUENCE: 6

```
Met Ile Leu Trp Asn Gly Thr Val Ala Leu Val Leu Thr Thr Val Val
1               5                   10                  15

Ser Ile His Ile Gly Tyr Ser Arg Thr Glu Met Lys Lys Ser Ile Asn
                20                  25                  30

Ala Gln Asn Lys Ile Glu Pro Ala Asn Leu Pro Lys Thr Met Gly Glu
```

-continued

```
            35                    40                    45
Ser Cys Thr Cys Ile Ile Pro Lys Lys Tyr Thr Ser Gly Ala Val Arg
 50                    55                    60

Gln Ile Gly Val Ser Tyr Ser Gly Phe Val Asp Glu Ser Tyr Thr Leu
 65                    70                    75                    80

Leu Ser Leu Phe Asp Asp Val Glu Gln Ile Glu Lys Asp Asn Arg Leu
                 85                    90                    95

Gln Thr Ala Ile Asp Val Val Arg Glu Gln Phe Gly Phe Leu Ala Ile
                100                   105                   110

Gln Lys Gly Thr Val Leu Thr Glu Gly Ser Arg Asn Ile Glu Arg Ser
                115                   120                   125

Lys Leu Ile Gly Gly His Ser Ala Gly Gly Leu Glu Gly Leu Lys
    130                   135                   140
```

<210> SEQ ID NO 7
<211> LENGTH: 440
<212> TYPE: PRT
<213> ORGANISM: Tn5252

<400> SEQUENCE: 7

```
Met Thr Pro His Leu Arg Leu Arg Leu Cys Val Met Ser Arg Ala Asp
 1               5                   10                   15

Asn Ser Ala Gly Leu Ile Leu Ala Ser Ser Pro Met Phe Lys Lys Val
                20                   25                   30

Phe Gly Lys Ser Asn Val Gly Arg Ser Tyr Asp Leu Pro Phe Asp Val
            35                   40                   45

Lys Thr Arg Lys Phe Ser Tyr Tyr Asn Ala Lys Lys Gln Gly Leu Pro
 50                   55                   60

Thr Thr Ile Asp Tyr Val Arg Tyr Ile Glu Glu Trp Ala Lys Ser Thr
 65                   70                   75                   80

Val Ile Val Pro Arg Glu Trp Ile Leu Thr Ile Ala Val Asn Met Glu
                85                   90                   95

Ile Gln Lys Ile Phe Gln Asp Phe Ala Ala Pro Asp Asp Ile Tyr Pro
                100                  105                  110

Tyr Ser Ile Asp Glu Gly Phe Ile Asp Leu Thr Ser Ser Leu Asn Tyr
            115                  120                  125

Phe Val Pro Asp Lys Ser Ile Ser Arg Lys Asp Lys Leu Asp Ile Ile
    130                  135                  140

Ser Ala Ala Ile Gln Lys Lys Ile Trp Arg Lys Thr Gly Ile Tyr Ser
145                  150                  155                  160

Thr Val Gly Met Ser Asn Ala Asn Pro Leu Leu Ala Lys Leu Ala Leu
                165                  170                  175

Asp Asn Glu Ala Lys Lys Thr Pro Thr Met Arg Ala Asn Trp Ser Tyr
            180                  185                  190

Glu Asp Val Glu Lys Lys Val Trp Thr Ile Pro Lys Met Thr Asp Phe
        195                  200                  205

Trp Gly Ile Gly Asn Arg Met Glu Lys Arg Leu His Asn Leu Gly Ile
    210                  215                  220

Phe Ser Ile Lys Glu Leu Ala Gln Ala Asn Pro Asp Leu Ile Lys Lys
225                  230                  235                  240

Glu Leu Gly Ile Met Gly Leu Glu Leu Trp Phe His Ala Asn Gly Ile
                245                  250                  255

Asp Glu Ser Asn Val His Lys Pro Tyr Lys Pro Lys Ser Lys Gly Ile
            260                  265                  270
```

```
Gly Asn Ser Gln Val Leu Pro Lys Asp Tyr Ile Lys Gln Arg Asp Ile
        275                 280                 285

Glu Ile Ile Leu Arg Glu Met Ala Glu Gln Val Ala Val Arg Leu Arg
290                 295                 300

Arg Ser Gly Lys Lys Ala Thr Val Val Ser Ile His Leu Gly Tyr Ser
305                 310                 315                 320

Lys Val Glu Gln Lys Arg Ser Ile Asn Thr Gln Met Lys Ile Glu Pro
                325                 330                 335

Thr Asn Gln Thr Ala Leu Leu Thr Asn Tyr Val Leu Lys Leu Phe His
                340                 345                 350

Thr Lys Tyr Thr Ser Gly Ala Ile Arg Asn Val Ala Val Asn Tyr Ser
            355                 360                 365

Gly Leu Val Asp Glu Ser Phe Gly Leu Ile Ser Leu Phe Asp Asp Ile
        370                 375                 380

Glu Lys Ile Glu Lys Glu Arg Leu Gln Ser Ala Ile Asp Ala Ile
385                 390                 395                 400

Arg Thr Glu Phe Gly Phe Thr Ser Leu Leu Lys Gly Asn Ala Leu Asp
                405                 410                 415

Gln Ala Ser Arg Thr Ile Ala Arg Ser Lys Leu Ile Gly Gly His Ser
                420                 425                 430

Ala Gly Gly Leu Asp Gly Leu Lys
            435                 440

<210> SEQ ID NO 8
<211> LENGTH: 488
<212> TYPE: PRT
<213> ORGANISM: Lactobacillus lactis

<400> SEQUENCE: 8

Met Gly Ile Gln Ile Leu Asn Asn Gln Phe Asp Tyr Ser Leu Glu Pro
1               5                   10                  15

Arg Arg Ala Ile Phe Phe Glu Asp Val Lys Ser Asn Tyr Ala Ser Ile
                20                  25                  30

Glu Cys Ile Glu Arg Gly Leu Asn Pro Leu Thr Thr Ser Leu Cys Val
            35                  40                  45

Met Ser Arg Ala Asp Asn Ser Asn Gly Leu Thr Leu Ala Ala Ser Pro
        50                  55                  60

Thr Phe Lys Lys Val Phe Gly Met Ser Asn Val Ser His Ser Lys Glu
65                  70                  75                  80

Leu Pro Phe Leu Val His Asn Arg Lys Phe Asn Tyr Arg Leu Trp Tyr
                85                  90                  95

Lys Lys His Thr Asp Ile Phe Gly Gln Thr Val Glu Pro Asp Pro Lys
                100                 105                 110

Tyr Ile Ser Glu Val Glu Arg Trp Ala Arg Gln Thr Tyr Ile Val Pro
            115                 120                 125

Pro Gln Met Leu Leu Tyr Ile Lys Lys Asn Leu Glu Val Ile Asn Ile
        130                 135                 140

Leu Arg Glu Ile Thr Ser Ile Asp Glu Ile His Ala Tyr Ser Ile Asp
145                 150                 155                 160

Glu Ser Cys Leu Asp Val Thr Glu Ser Leu Asp Phe Phe Pro Glu
                165                 170                 175

Ile Thr Asn Thr Tyr Glu Gln Met Asp Lys Leu Ala Gln Met Leu Gln
                180                 185                 190

Arg Lys Ile Tyr His Lys Thr Gly Leu Tyr Val Thr Ile Gly Met Gly
            195                 200                 205
```

```
Asp Asn Pro Leu Leu Ala Lys Leu Ala Met Asp Asn Tyr Ala Lys His
    210                 215                 220

Asn Thr Asn Met Arg Ala Leu Ile Arg Tyr Glu Asp Val Pro Ser Lys
225                 230                 235                 240

Val Trp Ser Ile Ser Asp Met Thr Asp Phe Trp Gly Ile Asn Val Arg
                245                 250                 255

Thr Glu Ala Arg Leu Asn Lys Leu Gly Ile His Ser Ile Lys Glu Leu
            260                 265                 270

Ala His Ala Asp Pro Asp Met Leu Lys Arg Glu Leu Gly Val Ile Gly
        275                 280                 285

Leu Gln Gln Phe Phe His Ala Asn Gly Ile Asp Glu Thr Arg Leu Thr
    290                 295                 300

Asp Lys Tyr Lys Arg Lys Ser Val Ser Phe Ser Asn Ser Gln Thr Leu
305                 310                 315                 320

Pro Arg Asp Tyr Thr Arg Lys Ser Glu Ile Gly Leu Ile Ile Asn Glu
                325                 330                 335

Met Ala Glu Gln Val Ala Val Arg Leu Arg Lys Ser Lys Lys Lys Ala
            340                 345                 350

Thr Asn Phe Ser Leu Phe Val Gly Phe Ser Met Ala Asp Tyr Lys Lys
        355                 360                 365

Ser Leu Ser Val Ser Arg Lys Ile Glu Pro Thr Ser Ser Thr Lys Asp
    370                 375                 380

Leu Gln Glu Ile Ala Thr Arg Leu Phe Asn Glu Lys Tyr Asp Glu Gly
385                 390                 395                 400

Ala Val Arg Arg Ile Gly Val Ser Ala Asn Asn Leu Ile Asp Glu Pro
                405                 410                 415

Tyr Gln Leu Ile Ser Leu Phe Asp Ser Asp Glu Glu Asn Glu Glu Thr
            420                 425                 430

Ile Lys Gln Lys Lys Asp Glu Ala Val Gln Glu Ala Leu Asp Ser Ile
        435                 440                 445

Arg Gln Lys Tyr His Phe Val Ser Val Gln Lys Ala Thr Val Leu Lys
    450                 455                 460

Lys Gly Ser Arg Ala Val Ala Arg Ser Lys Met Val Gly Gly His Ser
465                 470                 475                 480

Ala Gly Gly Leu Glu Gly Leu Asn
                485

<210> SEQ ID NO 9
<211> LENGTH: 442
<212> TYPE: PRT
<213> ORGANISM: Enterococcus faecalis

<400> SEQUENCE: 9

Met Asn Leu Thr Phe Asp Tyr Thr Lys Glu Pro Ser Arg Asp Val Phe
  1               5                  10                  15

Cys Ile Asp Val Lys Ser Phe Asn Ala Ser Val Glu Cys Val Glu Arg
                 20                  25                  30

Gly Leu Asp Pro Leu Lys Thr Met Leu Val Val Met Ser Asn Ser Glu
             35                  40                  45

Asn Ser Gly Gly Leu Val Leu Ala Ala Ser Pro Met Ala Lys Lys Val
         50                  55                  60

Leu Gly Ile Ser Asn Val Thr Arg Lys Asn Glu Val Pro Asp His Pro
 65                  70                  75                  80

Asn Leu Ile Ile Val Pro Pro Arg Met Lys Leu Tyr Met Lys Lys Asn
```

```
                    85                  90                  95
Gln Glu Ile Asn Asn Leu Tyr Asn Arg Phe Val Ser Asn Glu Asp His
                100                 105                 110
Ser Val Phe Ser Val Asp Glu Ser Phe Leu Asp Val Thr Ala Ser Leu
                115                 120                 125
Thr Tyr Phe Lys Cys Asp Thr Ala Tyr Lys Leu Ala Lys Ile Ile Gln
                130                 135                 140
Arg Val Ile Tyr Asn His Met Gly Leu Tyr Val Thr Ile Gly Ile Gly
145                 150                 155                 160
Glu Asn Pro Leu Leu Ala Lys Leu Ala Leu Asp Asn Glu Ala Lys Asn
                165                 170                 175
Ala Pro Gly Phe Val Ala Glu Trp Arg Tyr Glu Asp Val Pro Glu Lys
                180                 185                 190
Val Trp Pro Ile Ser Pro Leu Thr Glu Phe Cys Gly Ile Gly Asn Arg
                195                 200                 205
Met Ala Ala Arg Leu Lys Lys Leu Gly Ile Arg Ser Ile Tyr Asp Leu
                210                 215                 220
Ala His Ile Glu Pro Tyr Met Leu Lys Glu Arg Phe Gly Ile Met Gly
225                 230                 235                 240
Leu Gln Leu Tyr Ala His Ser Trp Gly Ile Asp Arg Ser Phe Leu Gly
                245                 250                 255
Gln Lys Ala Gly Arg Pro Thr Glu Lys Ser Phe Gly Asn Ser Gln Val
                260                 265                 270
Leu Pro Lys Asp Tyr Ala Asn Lys Glu Gln Ile Lys Leu Val Leu Lys
                275                 280                 285
Glu Leu Ser Asp Gln Val Ala Ser Arg Leu Arg Met Ala Ser Cys Gln
                290                 295                 300
Thr Thr Cys Val Ser Leu Phe Val Gly Tyr Ser Lys Gly Gln Thr Asp
305                 310                 315                 320
Lys Tyr Gly Gln Thr Gly Trp Arg Arg Gln Met Lys Val Glu Pro Ser
                325                 330                 335
Asn Asn Thr Lys Val Leu Thr Glu His Val Leu Arg Leu Phe Glu Glu
                340                 345                 350
Asn Tyr Ala Pro Gly Val Asp Val Arg Lys Leu Gly Val Ser Tyr Gly
                355                 360                 365
Arg Leu Val Trp Asn Lys Asn Leu Gln Leu Asp Leu Phe Pro Val Pro
                370                 375                 380
Glu Glu Gln Ile His Glu Thr Asp Met Tyr Phe Leu Ile Asp Lys Ile
385                 390                 395                 400
Arg Gln Lys Phe Gly Phe Lys Ala Leu Ile His Ala Ser Ser Leu Met
                405                 410                 415
Glu Gly Ala Thr Ala Ile Ser Arg Ala Ser Leu Val Gly Gly His Ala
                420                 425                 430
Gly Gly Thr Val Gly Leu Gly Thr Thr Lys
                435                 440

<210> SEQ ID NO 10
<211> LENGTH: 422
<212> TYPE: PRT
<213> ORGANISM: Escherichia coli

<400> SEQUENCE: 10

Met Phe Ala Leu Cys Asp Val Asn Ala Phe Tyr Ala Ser Cys Glu Thr
  1               5                  10                  15
```

-continued

Val Phe Arg Pro Asp Leu Trp Gly Lys Pro Val Val Leu Ser Asn
                20                  25                  30

Asn Asp Gly Cys Val Ile Ala Arg Asn Ala Glu Ala Lys Ala Leu Gly
            35                  40                  45

Val Lys Met Gly Asp Pro Trp Phe Lys Gln Lys Asp Leu Phe Arg Arg
        50                  55                  60

Cys Gly Val Val Cys Phe Ser Ser Asn Tyr Glu Leu Tyr Ala Asp Met
65                  70                  75                  80

Ser Asn Arg Val Met Ser Thr Leu Glu Glu Leu Ser Pro Arg Val Glu
                85                  90                  95

Ile Tyr Ser Ile Asp Glu Ala Phe Cys Asp Leu Thr Gly Val Arg Asn
            100                 105                 110

Cys Arg Asp Leu Thr Asp Phe Gly Arg Glu Ile Arg Ala Thr Val Leu
        115                 120                 125

Gln Arg Thr His Leu Thr Val Gly Val Gly Ile Ala Gln Thr Lys Thr
    130                 135                 140

Leu Ala Lys Leu Ala Asn His Ala Ala Lys Lys Trp Gln Arg Gln Thr
145                 150                 155                 160

Gly Gly Val Val Asp Leu Ser Asn Leu Glu Arg Gln Arg Lys Leu Met
                165                 170                 175

Ser Ala Leu Pro Val Asp Asp Val Trp Gly Ile Gly Arg Arg Ile Ser
            180                 185                 190

Lys Lys Leu Asp Ala Met Gly Ile Lys Thr Val Leu Asp Leu Ala Asp
        195                 200                 205

Thr Asp Ile Arg Phe Ile Arg Lys His Phe Asn Val Val Leu Glu Arg
210                 215                 220

Thr Val Arg Glu Leu Arg Gly Glu Pro Cys Leu Gln Leu Glu Glu Phe
225                 230                 235                 240

Ala Pro Thr Lys Gln Glu Ile Ile Cys Ser Arg Ser Phe Gly Glu Arg
                245                 250                 255

Ile Thr Asp Tyr Pro Ser Met Arg Gln Ala Ile Cys Ser Tyr Ala Ala
            260                 265                 270

Arg Ala Ala Glu Lys Leu Arg Ser Glu His Gln Tyr Cys Arg Phe Ile
        275                 280                 285

Ser Thr Phe Ile Lys Thr Ser Pro Phe Ala Leu Asn Glu Pro Tyr Tyr
    290                 295                 300

Gly Asn Ser Ala Ser Val Lys Leu Leu Thr Pro Thr Gln Asp Ser Arg
305                 310                 315                 320

Asp Ile Ile Asn Ala Ala Thr Arg Ser Leu Asp Ala Ile Trp Gln Ala
                325                 330                 335

Gly His Arg Tyr Gln Lys Ala Gly Val Met Leu Gly Asp Phe Phe Ser
            340                 345                 350

Gln Gly Val Ala Gln Leu Asn Leu Phe Asp Asp Asn Ala Pro Arg Pro
        355                 360                 365

Gly Ser Glu Gln Leu Met Thr Val Met Asp Thr Leu Asn Ala Lys Glu
    370                 375                 380

Gly Arg Gly Thr Leu Tyr Phe Ala Gly Gln Gly Ile Gln Gln Gln Trp
385                 390                 395                 400

Gln Met Lys Arg Ala Met Leu Ser Pro Arg Tyr Thr Thr Arg Ser Ser
                405                 410                 415

Asp Leu Leu Arg Val Lys
            420

```
<210> SEQ ID NO 11
<211> LENGTH: 9
<212> TYPE: DNA
<213> ORGANISM: Bacillus subtilis

<400> SEQUENCE: 11 aaattccac                                                                  9

<210> SEQ ID NO 12
<211> LENGTH: 9
<212> TYPE: DNA
<213> ORGANISM: Bacillus subtilis

<400> SEQUENCE: 12 atcacgcaa                                                                  9

<210> SEQ ID NO 13
<211> LENGTH: 9
<212> TYPE: DNA
<213> ORGANISM: Haemophilus influenzae

<400> SEQUENCE: 13 agacaggcc                                                                  9

<210> SEQ ID NO 14
<211> LENGTH: 9
<212> TYPE: DNA
<213> ORGANISM: Haemophilus influenzae

<400> SEQUENCE: 14 tgcctgata                                                                  9

<210> SEQ ID NO 15
<211> LENGTH: 9
<212> TYPE: DNA
<213> ORGANISM: Staphylococcus aureus

<400> SEQUENCE: 15 caaacaacc                                                                  9

<210> SEQ ID NO 16
<211> LENGTH: 10
<212> TYPE: DNA
<213> ORGANISM: Staphylococcus aureus

<400> SEQUENCE: 16
cacattgaat                                                                10

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide useful as a primer

<400> SEQUENCE: 17
agtatcatta atcactagtg c                                                   21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence:
```

-continued

Oligonucleotide useful as a primer

<400> SEQUENCE: 18
ttcttctggt actaaaagtg g                                    21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide useful as a primer

<400> SEQUENCE: 19
cttcacggtc taaatggctc g                                    21

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide useful as a primer

<400> SEQUENCE: 20
ccagtcacga cgttgtaaaa cg                                   22

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide useful as a primer

<400> SEQUENCE: 21
tagacaagac catcgcagat cct                                  23

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide useful as a primer

<400> SEQUENCE: 22
gtatcatgtc acttgctatg cc                                   22

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide useful as a primer

<400> SEQUENCE: 23
cctcaccgta actaatgaat gctc                                 24

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide useful as a primer

```
<400> SEQUENCE: 24
catagactgt aacgctctgg                                                       20

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide useful as a primer

<400> SEQUENCE: 25
cacttgtagg caagctaggt gt                                                    22

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide useful as a primer

<400> SEQUENCE: 26 catacccctat agtcggtgca g                                                    21

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide useful as a primer

<400> SEQUENCE: 27
ctggttctgg ttggcgactc                                                       20

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide useful as a primer

<400> SEQUENCE: 28
gtatcctggt actctcttgc tg                                                    22

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide useful as a primer

<400> SEQUENCE: 29
tctcactgca ccagaggtg                                                        19

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide useful as a primer
```

<400> SEQUENCE: 30
ggatacccag tctcctgaag                                                    20

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide useful as a primer

<400> SEQUENCE: 31
gactggcaat gctagcggc                                                     19

<210> SEQ ID NO 32
<211> LENGTH: 488
<212> TYPE: PRT
<213> ORGANISM: Staphylococcus epidermidis

<400> SEQUENCE: 32

Met Glu Gln Tyr Thr Ile Lys Phe Asn Gln Ile Asn His Lys Leu Thr
 1               5                  10                  15

Asp Leu Arg Ser Leu Asn Ile Asp His Leu Tyr Ala Tyr Gln Phe Glu
            20                  25                  30

Lys Ile Ala Leu Ile Gly Gly Asn Gly Thr Gly Lys Thr Thr Leu Leu
        35                  40                  45

Asn Met Ile Ala Gln Lys Thr Lys Pro Glu Ser Gly Thr Val Glu Thr
    50                  55                  60

Asn Gly Glu Ile Gln Tyr Phe Glu Gln Leu Asn Met Asp Val Glu Asn
65                  70                  75                  80

Asp Phe Asn Thr Leu Asp Gly Ser Leu Met Ser Glu Leu His Ile Pro
                85                  90                  95

Met His Thr Thr Asp Ser Met Ser Gly Gly Glu Lys Ala Lys Tyr Lys
            100                 105                 110

Leu Ala Asn Val Ile Ser Asn Tyr Ser Pro Ile Leu Leu Leu Asp Glu
        115                 120                 125

Pro Thr Asn His Leu Asp Lys Ile Gly Lys Asp Tyr Leu Asn Asn Ile
    130                 135                 140

Leu Lys Tyr Tyr Tyr Gly Thr Leu Ile Ile Val Ser His Asp Arg Ala
145                 150                 155                 160

Leu Ile Asp Gln Ile Ala Asp Thr Ile Trp Asp Ile Gln Glu Asp Gly
                165                 170                 175

Thr Ile Arg Val Phe Lys Gly Asn Tyr Thr Gln Tyr Gln Asn Gln Tyr
            180                 185                 190

Glu Gln Glu Gln Leu Glu Gln Arg Lys Tyr Glu Gln Tyr Ile Ser
        195                 200                 205

Glu Lys Gln Arg Leu Ser Gln Ala Ser Lys Ala Lys Arg Asn Gln Ala
    210                 215                 220

Gln Gln Met Ala Gln Ala Ser Ser Lys Gln Lys Asn Lys Ser Ile Ala
225                 230                 235                 240

Pro Asp Arg Leu Ser Ala Ser Lys Glu Lys Gly Thr Val Glu Lys Ala
                245                 250                 255

Ala Gln Lys Gln Ala Lys His Ile Glu Lys Arg Met Glu His Leu Glu
            260                 265                 270

Glu Val Glu Lys Pro Gln Ser Tyr His Glu Phe Asn Phe Pro Gln Asn
        275                 280                 285

```
Lys Ile Tyr Asp Ile His Asn Asn Tyr Pro Ile Ile Ala Gln Asn Leu
290                 295                 300

Thr Leu Val Lys Gly Ser Gln Lys Leu Leu Thr Gln Val Arg Phe Gln
305                 310                 315                 320

Ile Pro Tyr Gly Lys Asn Ile Ala Leu Val Gly Ala Asn Gly Val Gly
                325                 330                 335

Lys Thr Thr Leu Leu Glu Ala Ile Tyr His Gln Ile Glu Gly Ile Asp
                340                 345                 350

Cys Ser Pro Lys Val Gln Met Ala Tyr Arg Gln Leu Ala Tyr Glu
                355                 360                 365

Asp Met Arg Asp Val Ser Leu Leu Gln Tyr Leu Met Asp Glu Thr Asp
370                 375                 380

Ser Ser Glu Ser Phe Ser Arg Ala Ile Leu Asn Asn Leu Gly Leu Asn
385                 390                 395                 400

Glu Ala Leu Glu Arg Ser Cys Asn Val Leu Ser Gly Gly Glu Arg Thr
                405                 410                 415

Lys Leu Ser Leu Ala Val Leu Phe Ser Thr Lys Ala Asn Met Leu Ile
                420                 425                 430

Leu Asp Glu Pro Thr Asn Phe Leu Asp Ile Lys Thr Leu Glu Ala Leu
                435                 440                 445

Glu Met Phe Met Asn Lys Tyr Pro Gly Ile Ile Leu Phe Thr Ser His
                450                 455                 460

Asp Thr Arg Phe Val Lys His Val Ser Asp Lys Lys Trp Glu Leu Thr
465                 470                 475                 480

Gly Gln Ser Ile His Asp Ile Thr
                485

<210> SEQ ID NO 33
<211> LENGTH: 9
<212> TYPE: DNA
<213> ORGANISM: Bacillus subtilis

<400> SEQUENCE: 33 caaacgcat                                                             9

<210> SEQ ID NO 34
<211> LENGTH: 9
<212> TYPE: DNA
<213> ORGANISM: Bacillus subtilis

<400> SEQUENCE: 34 aatcataat                                                             9
```